United States Patent
Damask et al.

(10) Patent No.: US 10,066,267 B2
(45) Date of Patent: Sep. 4, 2018

(54) METHODS OF SELECTIVELY TREATING ASTHMA USING IL-13 ANTAGONISTS

(71) Applicants: Amy Damask, Somerville, MA (US); Steven Lewitzky, Boston, MA (US); Michael Rotte, Oberwil (CH)

(72) Inventors: Amy Damask, Somerville, MA (US); Steven Lewitzky, Boston, MA (US); Michael Rotte, Oberwil (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/302,348

(22) PCT Filed: Apr. 8, 2015

(86) PCT No.: PCT/IB2015/052551
§ 371 (c)(1),
(2) Date: Oct. 6, 2016

(87) PCT Pub. No.: WO2015/155710
PCT Pub. Date: Oct. 15, 2015

(65) Prior Publication Data
US 2017/0029894 A1    Feb. 2, 2017

Related U.S. Application Data

(60) Provisional application No. 61/978,604, filed on Apr. 11, 2014.

(51) Int. Cl.
*C12Q 1/6883* (2018.01)
*C07K 16/24* (2006.01)

(52) U.S. Cl.
CPC .......... *C12Q 1/6883* (2013.01); *C07K 16/244* (2013.01); *C07K 2317/34* (2013.01); *C07K 2317/51* (2013.01); *C07K 2317/565* (2013.01); *C07K 2317/76* (2013.01); *C07K 2317/92* (2013.01); *C07K 2317/94* (2013.01); *C12Q 2600/106* (2013.01); *C12Q 2600/118* (2013.01); *C12Q 2600/156* (2013.01); *C12Q 2600/158* (2013.01)

(58) Field of Classification Search
CPC ............ C12Q 1/6883; C12Q 2600/118; C12Q 2600/156; C12Q 2600/158; C12Q 2600/106; C07K 16/244; C07K 2317/34; C07K 2317/51; C07K 2317/565; C07K 2317/76; C07K 2317/92; C07K 2317/94
See application file for complete search history.

(56) References Cited

U.S. PATENT DOCUMENTS

2009/0214523 A1*  8/2009  Fung .................... C07K 16/244
                                                          424/133.1

FOREIGN PATENT DOCUMENTS

WO    2007/045477 A2    4/2007
WO    2011/156000 A2   12/2011

OTHER PUBLICATIONS

Liang W, et al. Zhonghua Yi Xue Yi Chuan Xue Za Zhi. (Feb. 2014):31(1):97-100. doi: 10.3760/cma.j.issn.1003-9406.2014.01.023.*
Rebecca E Slager et al. "IL-4 receptor polymorphisms predict reduction in asthma exacerbations during response to an antiiL-4 receptor antagonist", Journal of Allergy and Clinical Immunology, Elsevier. Amsterdam, NL, vol. 130, No. 2, Mar. 27, 2012, pp. 516-522.e4, XP028431308.

* cited by examiner

*Primary Examiner* — Robert S Landsman
(74) *Attorney, Agent, or Firm* — Jim Lynch

(57) ABSTRACT

The disclosure is directed to novel predictive methods and personalized therapies for treating asthma. Specifically, this disclosure relates to methods of treating a patient having asthma by selectively administering an IL-13 antagonist, on the basis of that patient being genetically predisposed to have a favorable response to treatment with the IL-13 antagonist. Also disclosed herein are transmittable forms of information, diagnostic methods, and kits useful in predicting the likelihood that a patient having asthma will respond to treatment with an IL-13 antagonist.

11 Claims, 9 Drawing Sheets

Specification includes a Sequence Listing.

Figure 1
Substitution Analysis:
Replacement of each residue from sequence MLSGFCPHKVSA against all 20 standard amino acids.

Figure 2    Exacerbation risk by genotype class for ANTIBODY 01951/G12-treated patients Figure 3    Exacerbation risk by genotype class for placebo-treated patients in the ANTIBODY 01951/G12 study Identification of two linkage disequilibrium blocks among IL4-Rα SNPs FIGURE 5: Results of Tests of Association Between SNP's and Asthma Endpoints at Week 24

| SNP (minor allele) | ACQ7 (Change from BL) | | FEV1 (% Change from BL) | | Serum IgE (% Change from BL) | | Asthma Exacerbations | |
|---|---|---|---|---|---|---|---|---|
| | Effect Size[1] (mean Δ with 95% CI) | P-value | Effect Size[2] (mean Δ with 95% CI) | P-value | Effect Size[2] (mean Δ with 95% CI) | P-value | Effect Size[3] (odds ratio with 95% CI) | P-value |
| rs1110470 (A) | -0.039 ± 0.23 | 0.73 | 5.4 ± 5.3 | 0.047 | +4.7 ± 13.9 | 0.51 | 0.15 (0.035,0.64) | 0.0056 |
| rs3024530 (G) | +0.142 ± 0.24 | 0.24 | +2.7 ± 5.9 | 0.37 | +0.6 ± 14.7 | 0.94 | 4.2 (1.2,14.6) | 0.015 |
| rs1805010 (G) | +0.172 ± 0.24 | 0.16 | +2.7 ± 5.9 | 0.38 | -0.6 ± 14.9 | 0.94 | 5.1 (1.3,19.9) | 0.010 |
| rs2239347 (C) | +0.023 ± 0.22 | 0.84 | +3.2 ± 5.4 | 0.25 | -0.2 ± 13.7 | 0.98 | 2.8 (0.9,8.7) | 0.066 |
| rs1805011 (C) | -0.106 ± 0.35 | 0.55 | +0.1 ± 8.5 | 0.98 | -4.6 ± 21.4 | 0.67 | NC[4] | 0.091 |
| rs1801275 (G) | -0.042 ± 0.25 | 0.74 | +2.9 ± 6.3 | 0.36 | -3.7 ± 15.6 | 0.64 | 0.30 (0.066,1.4) | 0.10 |
| rs8832 (A) | -0.049 ± 0.20 | 0.63 | +7.6 ± 4.7 | 0.0014 | -7.2 ± 12.5 | 0.26 | 3.8 (1.2,11.9) | 0.013 |
| rs1029489 (A) | -0.037 ± 0.20 | 0.72 | +7.0 ± 4.6 | 0.0033 | -6.3 ± 12.4 | 0.32 | 4.2 (1.4,12.9) | 0.0054 |
| rs4787956 (G) | -0.081 ± 0.22 | 0.47 | +7.2 ± 5.1 | 0.0064 | -5.4 ± 13.7 | 0.44 | 3.9 (1.3,11.7) | 0.0090 |

[1]Mean absolute change in ACQ7 from baseline to Week 24 associated with one additional copy of the minor allele
[2]Mean percent change in FEV1 or IgE from baseline to Week 24 associated with one additional copy of the minor allele
[3]Odds ratio for risk of experiencing an asthma exacerbation between baseline and Week 24 associated with one additional copy of the minor allele
[4]Not calculable because all patients with an exacerbation had the same genotype (AA)

FIGURE 6: Genotype Frequency distribution of IL-4Ra SNPs by Country

| SNP | Genotype | OAX576A2207 | ARG | BEL | CZE | DEU | POL | RUS | USA |
|---|---|---|---|---|---|---|---|---|---|
| | N= | 194 | 25 | 12 | 30 | 57 | 25 | 35 | 12 |
| rs1805010 | AA | | | | | | | | |
| | AG | 0.55 | 0.64 | 0.67 | 0.46 | 0.53 | 0.60 | 0.53 | 0.45 |
| | GG | 0.21 | 0.16 | 0.33 | 0.29 | 0.11 | 0.16 | 0.35 | 0.16 |
| rs8832 | GG | | | | | | | | |
| | AG | 0.48 | 0.48 | 0.50 | 0.50 | 0.47 | 0.60 | 0.46 | 0.25 |
| | AA | 0.22 | 0.16 | 0.33 | 0.21 | 0.23 | 0.12 | 0.23 | 0.42 |
| rs4787956 | AA | | | | | | | | |
| | AG | 0.51 | 0.56 | 0.67 | 0.50 | 0.47 | 0.52 | 0.51 | 0.42 |
| | GG | 0.12 | 0.04 | 0.25 | 0.18 | 0.14 | 0.04 | 0.11 | 0.17 |
| rs3024530 | AA | | | | | | | | |
| | AG | 0.55 | 0.64 | 0.67 | 0.46 | 0.51 | 0.60 | 0.54 | 0.50 |
| | GG | 0.21 | 0.16 | 0.33 | 0.29 | 0.12 | 0.16 | 0.31 | 0.17 |
| rs1029489 | GG | | | | | | | | |
| | AG | 0.45 | 0.48 | 0.46 | 0.43 | 0.46 | 0.48 | 0.43 | 0.33 |
| | AA | 0.20 | 0.16 | 0.36 | 0.21 | 0.18 | 0.12 | 0.23 | 0.33 |
| rs1110470 | GG | | | | | | | | |
| | AG | 0.31 | 0.36 | 0.42 | 0.39 | 0.25 | 0.24 | 0.37 | 0.25 |
| | AA | 0.50 | 0.48 | 0.50 | 0.46 | 0.51 | 0.56 | 0.49 | 0.50 |
| rs2239347 | AA | | | | | | | | |
| | AC | 0.51 | 0.48 | 0.42 | 0.46 | 0.56 | 0.48 | 0.54 | 0.42 |
| | CC | 0.25 | 0.28 | 0.50 | 0.29 | 0.12 | 0.28 | 0.31 | 0.17 |

FIGURE 7: Genotype Frequency Distribution of IL4-Ra SNPs by Ethnic Population

| SNP | Genotype | GAX576A2287 | ASW | CHB | CHD | GIH | LWK | MEX | MKK | TSI | CEU | HCB | JPT | YRI |
|---|---|---|---|---|---|---|---|---|---|---|---|---|---|---|
| | N= | 194 | 49 | 41 | 83 | 88 | 90 | 49 | 142 | 88 | 112 | 42 | 86 | 112 |
| rs1805010 | AA | 0.24 | 0.24 | 0.27 | 0.23 | 0.39 | 0.24 | 0.24 | 0.20 | 0.32 | 0.24 | 0.50 | 0.19 | 0.30 |
| | AG | 0.55 | 0.51 | 0.46 | 0.54 | 0.45 | 0.46 | 0.43 | 0.43 | 0.55 | 0.54 | 0.33 | 0.34 | 0.49 |
| | GG | 0.21 | 0.24 | 0.27 | 0.24 | 0.16 | 0.30 | 0.33 | 0.37 | 0.14 | 0.22 | 0.17 | 0.48 | 0.21 |
| rs8832 | GG | 0.30 | 0.00 | 0.30 | 0.25 | 0.35 | 0.00 | 0.27 | 0.03 | 0.32 | 0.26 | 0.24 | 0.19 | 0.02 |
| | AG | 0.48 | 0.33 | 0.44 | 0.52 | 0.49 | 0.24 | 0.53 | 0.27 | 0.53 | 0.47 | 0.43 | 0.39 | 0.25 |
| | AA | 0.22 | 0.67 | 0.37 | 0.24 | 0.16 | 0.76 | 0.20 | 0.69 | 0.16 | 0.28 | 0.33 | 0.42 | 0.73 |
| rs4787956 | AA | 0.37 | 0.43 | 0.17 | 0.24 | 0.40 | 0.37 | 0.30 | 0.38 | 0.38 | 0.39 | 0.26 | 0.16 | 0.41 |
| | AG | 0.51 | 0.49 | 0.44 | 0.50 | 0.45 | 0.56 | 0.52 | 0.52 | 0.50 | 0.43 | 0.44 | 0.41 | 0.43 |
| | GG | 0.12 | 0.08 | 0.39 | 0.26 | 0.15 | 0.08 | 0.18 | 0.10 | 0.13 | 0.18 | 0.30 | 0.43 | 0.16 |
| rs3024530 | AA | 0.25 | 0.22 | 0.27 | 0.26 | 0.39 | 0.26 | 0.24 | 0.17 | 0.30 | 0.23 | 0.49 | 0.19 | 0.27 |
| | AG | 0.55 | 0.53 | 0.49 | 0.55 | 0.43 | 0.42 | 0.44 | 0.54 | 0.57 | 0.54 | 0.30 | 0.31 | 0.50 |
| | GG | 0.21 | 0.24 | 0.24 | 0.19 | 0.18 | 0.32 | 0.32 | 0.28 | 0.14 | 0.23 | 0.21 | 0.50 | 0.24 |
| | N= | | | | | | | | | | 60 | 45 | 45 | 60 |
| rs1029489 | GG | 0.35 | | | | | | | | | 0.48 | 0.22 | 0.18 | 0.03 |
| | AG | 0.45 | | | | | | | | | 0.38 | 0.44 | 0.31 | 0.22 |
| | AA | 0.20 | | | | | | | | | 0.13 | 0.33 | 0.51 | 0.75 |
| rs1110470 | GG | 0.31 | | | | | | | | | 0.27 | 0.41 | 0.60 | 0.27 |
| | AG | 0.50 | | | | | | | | | 0.41 | 0.27 | 0.36 | 0.49 |
| | AA | 0.19 | | | | | | | | | 0.32 | 0.32 | 0.04 | 0.24 |
| rs2239347 | AA | 0.25 | | | | | | | | | 0.28 | 0.40 | 0.20 | 0.32 |
| | AC | 0.51 | | | | | | | | | 0.50 | 0.42 | 0.49 | 0.45 |
| | CC | 0.25 | | | | | | | | | 0.22 | 0.18 | 0.31 | 0.23 |

| Population | Description |
|---|---|
| ASW | African ancestry in Southwest USA |
| CHB | Han Chinese in Beijing, China (current) |
| CHD | Chinese in Metropolitan Denver, Colorado |
| GIH | Gujarati Indians in Houston, Texas |
| LWK | Luhya in Webuye, Kenya |
| MEX | Mexican ancestry in Los Angeles, California |

| Population | Description |
|---|---|
| MKK | Maasai in Kinyawa, Kenya |
| TSI | Toscan in Italy |
| CEU | Utah residents with Northern and Western European ancestry |
| HCB | Han Chinese in Beijing, China (obsolete) |
| JPT | Japanese in Tokyo, Japan |
| YRI | Yoruba in Ibadan, Nigeria |

FIGURE 8: Asthma Control Questionnaire -5 (ACQ5)

FIGURE 9: Asthma Control Questionnaire (AQLQ(S))

METHODS OF SELECTIVELY TREATING ASTHMA USING IL-13 ANTAGONISTS

SEQUENCE LISTING

The instant application contains a Sequence Listing which has been submitted electronically in ASCII format and is hereby incorporated by reference in its entirety. Said ASCII copy, created on Mar. 19, 2015, is named PAT056217-WO-PCT_SL.txt and is 40,804 bytes in size.

TECHNICAL FIELD

The disclosure is directed to predictive methods, personalized therapies, transmittable forms of information and methods for treating patients having asthma.

BACKGROUND OF THE DISCLOSURE

Asthma presents a major global health burden. Despite existing therapies, there is still significant unmet medical need in asthma, with an estimated 300 million people affected worldwide. The World Health Organization estimates that 15 million disability-adjusted life years are lost annually due to asthma, representing 1% of the total global burden. Annual worldwide deaths have been estimated at 250,000. Uncontrolled asthma has a prevalence of greater than 6 million patients worldwide.

Interleukin 13 (IL-13) is a cytokine produced by type 2 helper T cells (Th2), mast cells, eosinophils, and basophils (Kelly-Welch A, (2005), Sci STKE; 293:pcm 8) that promotes the production of inflammatory cytokines, up-regulates MHC class II and CD23 expression on monocytes, induces anti-CD40-dependent IgE class switch, and induces IgG and IgM synthesis in B cells (Joshi B H, (2006), Vitam Horm; 74:479-504). IL-13 has been shown to play a major role in the several biological processes, including airway hyper-responsiveness, allergic inflammation, tissue eosinophilia, parasite elimination, mast cell hyperplasia, IgE antibody synthesis, goblet cell metaplasia, tissue remodeling, and fibrosis (Belperio J A, (2002) Am J Respir Cell Mol Biol; 27(4): 419-427; Brombacher F (2000) Bioessays; 22: 646-656; Wynn T A, (2004), Immunol Rev; 201:156-67; Kolodsick J E, (2004), J Immunol; 172: 4068-4076). In particular, IL-13 has been shown to be a central mediator of allergic asthma in an animal model (Wills-Karp M, (1998), Science; 282: 2258-2261). This observation has been complemented by data showing that anti-IL-13 Ab inhibits asthma progression in mice (Yang G, (2005), J Pharmacol Exp Ther; 313(1): 8-15). IL-13 engages two related receptors on responsive cells, IL-13Rα1 and IL-13Rα2 (Wills-Karp M, (2008), Sci Signal; 1(51) pe55). IL-13Rα1 forms a complex with the IL-4Rα receptor subunit, which signals through the JAK/STAT pathway to phosphorylate STAT6, which acts as a transcription factor promoting the expression of eotaxin and other products involved in Th2-dependent inflammation. The second IL-13Rα2 receptor also binds IL-13, but does not appear to produce signals involved in allergy. Thus, the IL-13Rα1/IL-4Rα receptor complex provides a key common point in both IL-13 and IL-4 signaling pathways. See also Ingram and Kraft (2012) J Allergy Clin Immunol 130(4): 829-842.

WO05007699, WO07036745, WO12049278, and WO08106116 refer to anti-IL-13 antibodies and/or IL-13 antagonists for treatment of asthma.

There has been an ongoing search for biomarkers that define different asthma phenotypes (Wenzel S E (2012), Nat Med; 18(5): 716-725). WO12083132 refers to a method of identifying an asthma patient or a respiratory disorder patient who is likely to be responsive to treatment with a TH2 Pathway Inhibitor encompassing using an Eosinophilic Inflammation Diagnostic Assay.

Slager R E, (2012), J Allergy Clin Immunol; 130(2): 516-22, refer to a series of single nucleotide polymorphisms (SNPs) in the IL-4Rα receptor associated with a reduced risk of asthma exacerbations in patients treated with an IL-4 inhibitor. WO11156000 refers to use of methods and kits for determining the major allele in certain SNPs in the IL-4Rα receptor as an indication of likely response to IL-4/IL13 (IL-4 and IL-13) antagonist treatment, such as treatment with mutant human IL-4 protein.

BRIEF SUMMARY OF THE DISCLOSURE

There exists a need for identification of single nucleotide polymorphisms (SNP's) as being predictive of whether a patient having asthma will respond to a treatment with an IL-13 antagonist, as a pharmacogenomic biomarker approach to diagnosis and treatment of asthma. Provided herein are predictive methods and personalized therapies for patients having asthma that maximize the benefit and minimize the risk of IL-13 antagonism in these populations by identifying the patients likely to respond favorably, prior to treatment with an IL-13 antagonist. The inventive methods described herein are related to the discovery that patients with particular responsive genotypes had substantial reductions in the frequency of asthma exacerbations upon treatment antibody 01951/G12 (SEQ ID No. 14 and 16), a human IgG1/κ anti-IL-13 monoclonal antibody further described in WO2007/045477. The responsive genotypes in the patients are specific responsive alleles in SNPs of the IL-4Rα receptor gene and are provided in Table 1.

TABLE 1

| AIR marker | SNP | 5' Nucleotide sequence | SEQ ID NO: | RefSNP alleles |
|---|---|---|---|---|
| 1 | rs1110470 | GAAGGTTGGCAGGCCAGGGACAACA[C/T]CGTCTGCCAAGCCATGGCAGTAGAC | 22 | C/T (REV) |
| 2 | rs3024530 | TAAGGTATTTTTGTTATAGCAGCCT[A/G]TATGGACTAAGCTGACTTGTAACGT | 23 | A/G (FWD) |
| 3 | rs1805010 | CTGTGTCTGCAGAGCCCACACGTGT[A/G]TCCCTGAGAACAACGGAGGCGCGGG | 24 | A/G (FWD) |
| 4 | rs2239347 | ACCCCAGGTCCCATATGTCCAGAGA[G/T]TGTCCCTCCAATGGGAATGTGAGGA | 25 | G/T (REV) |

TABLE 1-continued

| AIR marker | SNP | 5' Nucleotide sequence | SEQ ID NO: | RefSNP alleles |
|---|---|---|---|---|
| 5 | rs1805011 | AGGGATGACTTCCAGGAGGGAAGGG[A/C]GGGCATTGTGGCCCGGCTAACAGAG | 26 | A/C (FWD) |
| 6 | rs1801275 | GTCTCGGCCCCCACCAGTGGCTATC[A/G]GGAGTTTGTACATGCGGTGGAGCAG | 27 | A/G (FWD) |
| 7 | rs8832 | GCAACAGAGGACATGAAAAATTGCT[A/G]TGACTAAAGCAGGGACAATTTGCTG | 28 | A/G (FWD) |
| 8 | rs1029489 | CTTGTATGGGGAACCCAAACCCAGA[C/T]GGCAAGTTTCTTAACCTCTTGCATC | 29 | C/T (REV) |
| 9 | rs4787956 | GCTTATGTCATCCTGACACCTACGC[A/G]GATGTCGGCTCGAATCCACTTTGCC | 30 | A/G (FWD) |

Table 1 sets forth the SNP nucleotide sequences for the IL-4Rα receptor as designated by the corresponding rs number. The SNP sequences are also provided in the dbSNP database as referenced in further detail below. The alternative alleles are shown in brackets. The inventive responsive allele is shown in Table 1 in bold type, and respectively designated as anti-IL-13 response marker ("AIR marker" hereinafter). Accordingly, the designation AIR marker is in reference to the responsive allele only and excludes the non-responsive allele. In this regard, it is further recognized that a patient can be homozygous or heterozygous with respect to a particular AIR marker. Thus, for example, a patient that is determined to be homozygous for AIR marker 3, has an AA genotype for the rs1805010 SNP, whereas the patient that is heterozygous for AIR marker 3 has an AG genotype for this SNP. In the inventive methods of the invention, a patient is positive for a particular AIR marker, and therefore for the responsive allele, where the patient is homozygous or heterozygous for the responsive allele. A patient that is negative for a particular AIR marker is homozygous for the non-responsive allele. For example, a patient that is negative for AIR marker 3 has a GG for the rs1805010 SNP.

The invention provides a method of selectively treating a patient having asthma, comprising identifying a patient having at least one AIR marker selected from the group consisting of AIR marker—1, 2, 3, 4, 5, 6, 7, 8, and 9, and thereafter administering a therapeutically effective amount of an IL-13 antagonist to the patient.

In one embodiment, the identification comprises assaying a biological sample from the patient for the presence of at least one AIR marker selected from said group.

In another embodiment, the invention provides a method of selectively treating a patient having asthma, comprising:
i) assaying a biological sample from the patient for the presence or absence of at least one AIR marker selected from said group consisting of AIR marker—1, 2, 3, 4, 5, 6, 7, 8, and 9;
ii) detecting the presence of at least one AIR marker selected from said group in said sample and thereby determining that the patient is positive for said AIR marker, and
iii) selectively administering a therapeutically effective amount of an IL-13 antagonist to the patient that is positive.

In another embodiment, the inventive methods further comprise determining whether said AIR marker is present in homozygous or heterozygous form wherein the presence of the at least one AIR marker in homozygous form is determinative that the patient is positive for said AIR marker.

In another embodiment, the AIR marker is selected from the group consisting of Air marker 3 and Air marker 10.

In another embodiment, the inventive selective treatment methods further comprise determining whether the patient is homozygous or heterozygous for said AIR marker, and selectively administering a therapeutically effective amount of an IL-13 antagonist to the patient that is homozygous for one of AIR marker 3 and Air marker 10 and heterozygous for the other; homozygous for both AIR markers 3 and 10; or homozygous for AIR marker 3.

In other embodiments, the invention is directed to methods for predicting the likelihood that a patient having asthma will respond to treatment with an IL-13 antagonist. In one such embodiment, the methods comprise assaying a biological sample from the patient for the presence or absence of at least one AIR marker selected from the group consisting of AIR marker—1, 2, 3, 4, 5, 6, 7, 8, and 9, wherein:
a) the presence of the at least one AIR marker is indicative of an increased likelihood that the patient will respond to treatment with the IL-13 antagonist; and
b) the absence of the at least one AIR marker is indicative of a decreased likelihood that the patient will respond to treatment with the IL-13 antagonist.

In another such embodiment, the methods comprise the step of assaying a biological sample from the patient for the presence or absence of at least one AIR marker selected from the group consisting of AIR marker—1, 2, 3, 4, 5, 6, 7, 8, and 9 in homozygous form, wherein:
a) the presence of the at least one AIR marker in homozygous form is indicative of an increased likelihood that the patient will respond to treatment with the IL-13 antagonist; and
b) the absence of the at least one AIR marker in homozygous form is indicative of a decreased likelihood that the patient will respond to treatment with the IL-13 antagonist.

In another such embodiment, the methods comprise the steps of:
a) assaying a biological sample from the patient for the presence or absence of at least one AIR marker, and
b) determining whether said AIR marker is present in homozygous or heterozygous form, wherein
the presence of the at least one AIR marker in homozygous form is indicative of an increased likelihood that the patient will respond to treatment with the IL-13 antagonist, wherein said at least one AIR marker is selected from the group consisting of:

i) AIR marker 3 and 7 each present in homozygous form;
ii) AIR marker 3 present in homozygous form and AIR marker 7 in heterozygous form;
iii) AIR marker 7 present in homozygous form and AIR marker 3 in heterozygous form; and
iv) AIR marker 3 in homozygous form.

In another embodiment, the step of assaying comprises assaying the biological sample for a nucleic acid product of the at least one AIR marker, or a polypeptide product of the at least one AIR marker. In another embodiment, the step of assaying comprises assaying the biological sample for a genomic sequence of the at least one AIR marker.

In another embodiment, the biological sample is selected from the group consisting of blood, serum, feces, plasma, urine, tear, saliva, and a tissue sample.

In another embodiment, the step of assaying comprises a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, SNPLex®, capillary electrophoresis, Southern Blot, immunoassays, immunohistochemistry, ELISA, flow cytometry, Western blot, HPLC, and mass spectrometry.

In other embodiments, the invention is directed to methods for producing a transmittable form of information for predicting the responsiveness of a patient having asthma to treatment with an IL-13 antagonist, comprising determining an increased likelihood of the patient responding to treatment with the IL-13 antagonist according to the inventive methods set forth above; and recording the result of the determining step on a tangible or intangible media form for use in transmission.

In another embodiment, the IL-13 antagonist utilized in the inventive method competes with antibody 01951/G12 (SEQ ID No. 14 and 16) for binding to IL-13 under conditions that promote the competition.

In another embodiment, the IL-13 antagonist is a polypeptide or a fragment thereof, an antibody or an antigen binding fragment thereof, a Fab, an ScFv.

In another embodiment, the IL-13 antagonist is an antibody or a fragment thereof that binds to an epitope of IL-13 comprising residues FCPHKV (SEQ ID NO: 67) set forth as residues 103 to 107 of SEQ ID NO: 1.

In another embodiment, the IL-13 antagonist is antibody 01951/G12 (SEQ ID No. 14 and 16).

In another embodiment, the IL-13 antagonist is an antibody administered at a dose of about 50-1000 mg i.v. every four weeks (q4wk). In another embodiment, the IL-13 antagonist is an antibody administered at a dose of about 75 mg, or 750 mg i.v. every four weeks.

In another embodiment, the IL-13 antagonist has a $K_D$ of about 100-200 pM. In other embodiments the antagonist has a higher affinity for IL-13 and exhibits a $K_D$ of less than 100 pM. In a particular embodiment the IL-13 antagonist is an antibody that has a $K_D$ of about 140 pM.

In another embodiment, the IL-13 antagonist has an in vivo half-life of about 15-30 days, or about 21 days.

In another embodiment, the IL-13 antagonist is an antibody selected from the group consisting of:

i. an antibody comprising one or more of the CDRs selected from the list consisting of: (a) the $V_H$ CDR1s shown in SEQ ID NOs: 2 or 5 (b) the $V_H$ CDR2s shown in SEQ ID NOs: 3 or 6, (c) the $V_H$ CDR3s shown in SEQ ID NOs: 4 or 7 (d) the $V_L$ CDR1s shown in SEQ ID NOs: 8 or 11, (e) the $V_L$ CDR2s shown in SEQ ID NOs: 9 or 12, (f) the $V_L$ CDR3s shown in SEQ ID NOs: 10 or 13;

ii. an antibody comprising a heavy chain variable region CDR1 of SEQ ID NO: 2; a heavy chain variable region CDR2 of SEQ ID NO: 3; a heavy chain variable region CDR3 of SEQ ID NO: 4; a light chain variable region CDR1 of SEQ ID NO: 8; a light chain variable region CDR2 of SEQ ID NO: 9; and a light chain variable region CDR3 of SEQ ID NO: 10;

iii. an antibody comprising a heavy chain variable region CDR1 of SEQ ID NO: 5; a heavy chain variable region CDR2 of SEQ ID NO: 6; a heavy chain variable region CDR3 of SEQ ID NO: 7; a light chain variable region CDR1 of SEQ ID NO: 11; a light chain variable region CDR2 of SEQ ID NO: 12; and a light chain variable region CDR3 of SEQ ID NO: 13, iv. an antibody comprising a heavy chain variable region as recited in SEQ ID NO: 14 and a light chain variable region as recited in SEQ ID NO: 16, v. an antibody comprising a heavy chain as recited in SEQ ID NO: 20 and a light chain as recited in SEQ ID NO: 18.

In another embodiment, the IL-13 antagonist is a human antibody.

In a particular embodiment of the invention, the IL-13 antagonist is an antibody that prevents IL-13 binding to IL-13 Rα1. In another, the IL-13 antagonist prevents IL-13 binding to IL-13 Rα1, but allows binding to IL1-13 Rα2 also known as the decoy receptor.

In another embodiment, the patient has moderate asthma, and in another, severe asthma.

Additional methods, uses, and kits are provided in the following description and appended claims. Further features, advantages and aspects of the present disclosure will become apparent to those skilled in the art from the following description and appended claims.

BRIEF DESCRIPTION OF THE DRAWINGS

FIG. 1 depicts substitution analysis for binding of ANTIBODY 01951/G12 to selected IL-13 residues. Figure discloses SEQ ID NO: 33.

FIG. 5 depicts the results of tests of association between SNPs and asthma endpoints at week 24.

FIG. 6 depicts the genotype frequency distribution of IL-4 SNPs by country.

FIG. 7 depicts the distribution of IL-4 SNPs by ethnic population.

FIG. 8 depicts the asthma control questionnaire ACQ5.

FIG. 9 depicts the asthma control questionnaire AQLQ(S).

DETAILED DESCRIPTION OF THE DISCLOSURE

Figure 2:
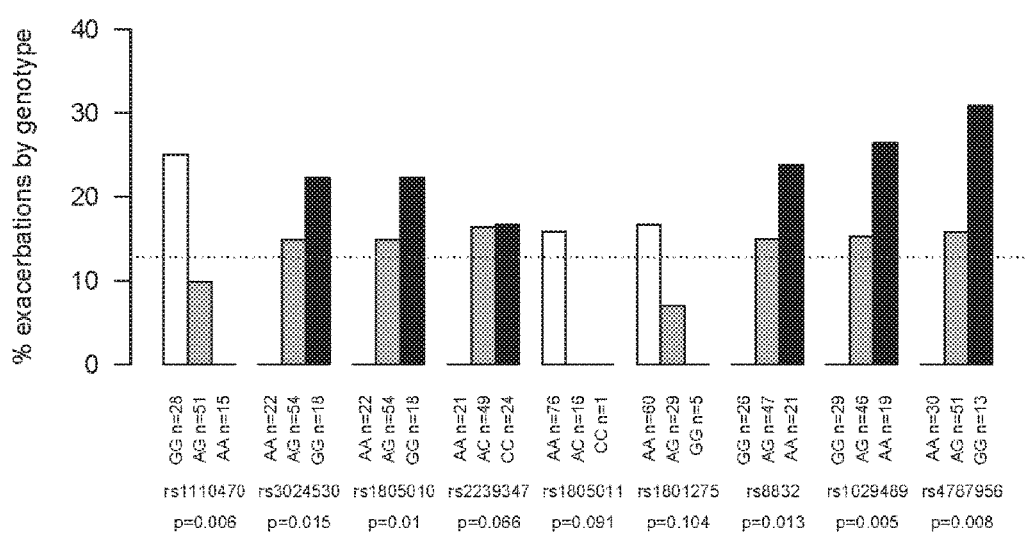
FIG. 2 depicts asthma exacerbation risk by genotype class for ANTIBODY 01951/G12-treated patients.

It is envisioned that testing subjects for the presence of at least one of the aforementioned response alleles (AIR markers) will be useful in a variety of pharmaceutical products and methods that involve identifying asthma patients, including severe to moderate asthma patients who are more likely to respond to IL-13 antagonsim and in helping physicians decide whether to prescribe IL-13 antagonists (e.g. antibody 01951/G12) to those patients or whether to prescribe an alternative pharmaceutical agent.

Accordingly, in one aspect the invention provides methods of treating a patient having asthma by administering to the patient a therapeutically effective amount of an IL-13 antagonist, e.g., an IL-13 antibody, such as antibody 01951/G12, based on certain aspects of the patient's genotypic profile. In a related aspect, the invention further provides methods of identifying a patient having asthma who is more likely to respond to treatment of with an IL-13 antagonist, e.g., an IL-13 antibody, such as antibody 01951/G12, based on certain aspects of the patient's genotypic profile. In a further related aspect, the invention provides methods of determining the likelihood that a patient having asthma will respond to treatment with an IL-13 antagonist, e.g., an IL-13 antibody, such as antibody 01951/G12, based on certain aspects of the patient's genotypic profile. In another related aspect, the invention provides various methods of selectively treating a patient having asthma.

The inventive methods described herein encompass utilizing at least one AIR marker selected from a group consisting of nine specified AIR markers set forth herein. The term "at least one AIR marker" contemplates that one, two, three, four, 5, six, seven, eight, or nine AIR markers can be combined and utilized in the methods of the invention. Furthermore, each AIR marker member of such combinations can be in heterozygous or homozygous form. Particular embodiments of the invention set forth specific combinations of nine AIR markers (AIR markers—1 to 9) and further specify desired zygosities with respect to a particular AIR marker.

The term "comprising" encompasses "including" as well as "consisting," e.g. a composition "comprising" X may consist exclusively of X or may include something additional, e.g., X+Y.

The term "about" in relation to a numerical value x means +/−10% unless the cotext dictates otherwise.

The term "assaying" is used to refer to the act of identifying, screening, probing, testing measuring or determining, which act may be performed by any conventional means. For example, a sample may be assayed for the presence of a particular genetic or protein marker by using an ELISA assay, a Northern blot, imaging, serotyping, cellular typing, gene sequencing, phenotyping, haplotyping, immunohistochemistry, western blot, mass spectrometry, etc. The term "detecting" (and the like) means the act of extracting particular information from a given source, which may be direct or indirect. In some embodiments of the predictive methods disclosed herein, the presence of a given thing (e.g., allele, level of protein, etc.) is detected in a biological sample indirectly, e.g., by querying a database. The terms "assaying" and "determining" contemplate a transformation of matter, e.g., a transformation of a biological sample, e.g., a blood sample or other tissue sample, from one state to another by means of subjecting that sample to physical testing.

The term "obtaining" means to procure, e.g., to acquire possession of in any way, e.g., by physical intervention (e.g., biopsy, blood draw) or non-physical intervention (e.g, transmittal of information via a server), etc.

The phrase "assaying a biological sample . . . " and the like, is used to mean that a sample may be tested (either directly or indirectly) for either the presence of a given AIR marker. It will be understood that, in a situation where the presence of a substance denotes one probability and the absence of a substance denotes a different probability, then either the presence or the absence of such substance may be used to guide a therapeutic decision. For example, one may determine if a patient has AIR marker by determining the actual existence of particular response allele in the patient or by determining the absence of the particular response allele in the patient. In both such cases, one has determined whether the patient has the presence of the AIR marker. The disclosed methods involve, inter alia, determining whether a particular individual has an AIR marker. This determination is undertaken by identifying whether the patient has one or more of the AIR markers disclosed in Table 1 set forth above. Each of these determinations (i.e., presence or absence), on its own, provides the allelic status of the patient and thus each of these determinations equally provide an indication of whether a particular individual would or would not respond more favorably to IL-13 antagonism. To provide an indication of increased responsiveness for an asthma patient, a biological sample need only be assayed for one or more AIR marker set forth in Table 1.

"IL-13 antagonist" as used herein refers to a molecule that antagonizes (e.g., reduces, inhibits, decreases, delays, eliminates) IL-13 function, expression and/or signalling by blocking the binding of IL-13 to the IL-13 receptor complex. In a particular embodiment of the invention, the IL-13 antagonist prevents IL-13 binding to IL-13 R$\alpha$1. In another, the IL-13 antagonist prevents binding to IL-13 R$\alpha$1, but allows binding to IL1-13 R$\alpha$2 (also known as the decoy receptor). See Ingram and Kraft (2012) J Allergy Clin Immunol 130(4): 829-842.

The binding reaction may be shown by standard methods (qualitative or quantitative assays) including, for example, a binding assay, competition assay or a bioassay for determining the inhibition of IL-13 binding to its receptor or any kind of binding assays, with reference to a negative control test in which an antibody of unrelated specificity, but ideally of the same isotype, e.g., an anti-CD25 antibody, is used. Such methods include those set forth below in the EXAMPLES.

The term "antibody" as referred to herein includes whole antibodies and any antigen-binding portion or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed hypervariable regions or complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody as used herein, refers to fragments of an antibody that retain the ability to specifically bind to an antigen (e.g., IL-13). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated CDR. Exemplary antigen binding sites include the CDRs set forth in SEQ ID NOs:1-6 and 11-13 (Table 2), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art.

An "isolated antibody", as used herein, refers to an antibody that is substantially free of other antibodies having different antigenic specificities (e.g., an isolated antibody that specifically binds IL-13 is substantially free of antibodies that specifically bind antigens other than IL-13). The term "monoclonal antibody" or "monoclonal antibody composition" as used herein refer to a preparation of antibody molecules of single molecular composition. The term "human antibody", as used herein, is intended to include antibodies having variable regions in which both the framework and CDR regions are derived from sequences of human origin. A "human antibody" need not be produced by a human, human tissue or human cell. The human antibodies of the disclosure may include amino acid residues not encoded by human sequences (e.g., mutations introduced by random or site-specific mutagenesis in vitro, by N-nucleotide addition at junctions in vivo during recombination of antibody genes, or by somatic mutation in vivo). In some embodiments of the disclosed methods, the IL-13 antagonist is a human antibody, an isolated antibody, and/or a monoclonal antibody.

The term "$K_D$" is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The term "affinity" refers to the strength of interaction between antibody and antigen at single antigenic sites. Within each antigenic site, the variable region of the antibody arm interacts through weak non-covalent forces with antigen at numerous sites; the more interactions, the stronger the affinity. Standard assays to evaluate the binding affinity of the antibodies toward IL-13 of various species are known in the art, including for example, ELISAs, western blots and RIAs. The binding kinetics (e.g., binding affinity) of the antibodies also can be assessed by standard assays known in the art, such as by Biacore analysis.

An antibody that "inhibits" one or more of these IL-13 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-13 activity affects a statistically significant decrease, e.g., by at least about 10% of the measured parameter, by at least 50%, 80% or 90%, and in certain embodiments of the disclosed methods, the IL-13 antibody used may inhibit greater than 95%, 98% or 99% of IL-13 functional activity.

The term "derivative", unless otherwise indicated, is used to define amino acid sequence variants, and covalent modifications (e.g., pegylation, deamidation, hydroxylation, phosphorylation, methylation, etc.) of an IL-13 antagonist (e.g., IL-13 antibody or antigen-binding portion thereof), e.g., of a specified sequence (e.g., a variable domain). A "functional derivative" includes a molecule having a qualitative biological activity in common with the disclosed IL-13 antagonists. A functional derivative includes fragments and peptide analogs of an IL-13 antagonist as disclosed herein. Fragments comprise regions within the sequence of a polypeptide according to the present disclosure, e.g., of a specified sequence. Functional derivatives of the IL-13 antagonists disclosed herein preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-13 binding molecules disclosed herein (e.g., the $V_H$ and/or $V_L$ sequences of Table 2), and substantially retain the ability to bind human IL-13.

The phrase "substantially identical" means that the relevant amino acid or nucleotide sequence (e.g., $V_H$ or $V_L$ domain) will be identical to or have insubstantial differences (e.g., through conserved amino acid substitutions) in comparison to a particular reference sequence. Insubstantial differences include minor amino acid changes, such as 1 or 2 substitutions (e.g., conservative substitutions, such as swapping a serine for a threonine, or substitutions at positions not involved in antibody activity, structural integrity, complement fixation, etc.) in a 5 amino acid sequence of a specified region (e.g., $V_H$ or $V_L$ domain). In the case of antibodies, the second antibody has the same specificity and has at least 50% of the affinity of the same. Sequences substantially identical (e.g., at least about 85% sequence identity) to the sequences disclosed herein are also part of this disclosure. In some embodiments, the sequence identity of a derivative anti-IL-13 antibody (can be about 90% or greater, e.g., 90%, 91%, 92%, 93%, 94%, 95%, 96%, 97%, 98%, 99% or higher relative to the disclosed sequences.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444-453); or the algorithm of Meyers et al. ((1988) Comput. Appl. Biosci., 4: 11-17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4: 11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The phrase "amino acid sequence variant" refers to molecules with some differences in their amino acid sequences as compared to the sequences according to the present disclosure. Amino acid sequence variants of an IL-13 antagonist polypeptide according to the present disclosure, e.g., of a specified sequence, still have the ability to bind the human IL-13 or. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "pharmaceutically acceptable" means a nontoxic material that does not interfere with the effectiveness of the biological activity of the active ingredient(s).

The term "administering" in relation to a compound, e.g., an IL-13 binding molecule or another agent, is used to refer to delivery of that compound to a patient by any route.

As used herein, a "therapeutically effective amount" refers to an amount of an IL-13 antagonist, (e.g., anti-IL-13 antibody or antigen-binding portion thereof) that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., an IL-13 antagonist, administered alone, the term refers to that ingredient alone. When applied to a combination, the term refers to combined amounts of the active ingredients that result in the therapeutic effect, whether administered in combination, serially or simultaneously.

The term "treatment" or "treat" refer to both prophylactic or preventative treatment (as the case may be) as well as curative or disease modifying treatment, including treatment of a patient at risk of contracting the disease or suspected to have contracted the disease as well as patients who are ill or have been diagnosed as suffering from a disease or medical condition, and includes suppression of clinical relapse or exacerbation. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment.

The phrase "responds to treatment" is used to mean that a patient, upon being delivered a particular treatment, e.g., an IL-13 antagonist, shows a clinically meaningful benefit from said treatment. In the case of asthma, including severe to moderate asthma, such criteria include reduction in exacerbations. The phrase "respond to treatment" is meant to be construed comparatively, rather than as an absolute response. For example, an asthma patient having an AIR marker is predicted to have more benefit from treatment with an IL-13 antagonist than a patient who does not have the AIR marker. These carriers of AIR markers respond more favorably to treatment with the IL-13 antagonist, and "respond to treatment" with an IL-13 antagonist. In certain embodiments of the invention, the patient that responds to treatment with an IL-13 antagonist according to the methods disclosed herein, has determinably reduced exacerbation of asthma for at least 24 weeks, at least 24-52 weeks, at least 52 weeks, or longer. In particular embodiments of the invention, the reduction in exacerbations is at least 50%, at least 60%, at least 70%, at least 80%, at least 90%, or 100% in the patient that responds to treatment with an IL-13 antagonist according to the methods disclosed herein.

The phrase "receiving data" is used to mean obtaining possession of information by any available means, e.g., orally, electronically (e.g., by electronic mail, encoded on diskette or other media), written, etc.

As used herein, "selecting" and "selected" in reference to a patient is used to mean that a particular patient is specifically chosen from a larger group of patients on the basis of (due to) the particular patient having a predetermined criteria, e.g., the patient has an AIR marker. Similarly, "selectively treating" refers to providing treatment to a patient having a particular disease, where that patient is specifically chosen from a larger group of patients on the basis of the particular patient having a predetermined criteria, e.g., an asthma patient specifically chosen for treatment due to the patient having a AIR marker. Similarly, "selectively administering" refers to administering a drug to a patient that is specifically chosen from a larger group of patients on the basis of (due to) the particular patient having a predetermined criteria, e.g., a particular genetic or other biological marker. By selecting, selectively treating and selectively administering, it is meant that a patient is delivered a personalized therapy based on the patient's particular biology, rather than being delivered a standard treatment regimen based solely on the patient having a particular disease. Selecting, in reference to a method of treatment as used herein, does not refer to fortuitous treatment of a patient that has an AIR marker, but rather refers to the deliberate choice to administer an IL-13 antagonist to a patient based on the patient having an AIR marker. Thus, selective treatment differs from standard treatment, which delivers a particular drug to all patients, regardless of their allelic status.

As used herein, "predicting" indicates that the methods described herein provide information to enable a health care provider to determine the likelihood that an individual having asthma will respond to or will respond more favorably to treatment with an IL-13 antagonist. It does not refer to the ability to predict response with 100% accuracy. Instead, the skilled artisan will understand that it refers to an increased probability.

As used herein, "likelihood" and "likely" is a measurement of how probable an event is to occur. It may be used interchangably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage increase) with the IL-13 antagonist or the patient may not be treated (or treatment discontinued, or treatment proceed with a lowered dose) with the IL-13 antagonist.

The phrase "increased likelihood" refers to an increase in the probability that an event will occur. For example, some methods herein allow prediction of whether a patient will display an increased likelihood of responding to treatment with an IL-13 antagonist or an increased likelihood of responding better to treatment with an IL-13 antagonist in comparison to a patient having asthma who does not have an AIR.

As used herein "SNP" refers to "single nucleotide polymorphism". A single nucleotide polymorphism is a DNA sequence variation occurring when a single nucleotide in the genome (or other shared sequence) differs between members of a biological species or paired chromosomes in an individual. Most SNPs have only two alleles, and one is usually more common in the population. A SNP may be present in an exon or an intron of a gene, an upstream or downstream untranslated region of a gene, or in a purely genomic location (i.e., non-transcribed). When a SNP occurs in the coding region of a gene, the SNP may be silent (i.e., a synonymous polymorphism) due to the redundancy of the genetic code, or the SNP may result in a change in the sequence of the encoded polypeptide (i.e., a non-synonymous polymorphism). In the instant disclosure, SNPs are identified by their Single Nucleotide Polymorphism Database (dbSNP) rs number, e.g. rs1805010. The dbSNP is a free public archive for genetic variation within and across different species developed and hosted by the National Center for Biotechnology Information (NCBI) in collaboration with the National Human Genome Research Institute (NHGRI).

A polymorphic site, such as a SNP, is usually preceded by and followed by conserved sequences in the genome of the population of interest and thus the location of a polymorphic site can often be made in reference to a consensus nucleic acid sequence (e.g., of thirty to sixty nucleotides) that bracket the polymorphic site, which in the case of a SNP is commonly referred to as the "SNP context sequence". Context sequences for the SNPs disclosed herein may be found in the NCBI SNP database available at: www.ncbi.nlm.nih.gov/snp. Alternatively, the location of the polymorphic site may be identified by its location in a reference sequence (e.g., GeneBank deposit) relative to the start of the gene, mRNA transcript, BAC clone or even relative to the initiation codon (ATG) for protein translation. The skilled artisan understands that the location of a particular polymorphic site may not occur at precisely the same position in a reference or context sequence in each individual in a population of interest due to the presence of one or more insertions or deletions in that individual's genome as compared to the consensus or reference sequence. It is routine for the skilled artisan to design robust, specific and accurate assays for detecting the alternative alleles at a polymorphic site in any given individual, when the skilled artisan is provided with the identity of the alternative alleles at the polymorphic site to be detected and one or both of a reference sequence or context sequence in which the polymorphic site occurs. Thus, the skilled artisan will understand that specifying the location of any polymorphic site described herein by reference to a particular position in a reference or context sequence (or with respect to an initiation codon in such a sequence) is merely for convenience and that any specifically enumerated nucleotide position literally includes whatever nucleotide position the same polymorphic site is actually located at in the same locus in any individual being tested for the genetic marker of the invention using any of the genotyping methods described herein or other genotyping methods known in the art.

In addition to SNPs, genetic polymorphisms include translocations, insertions, substitutions, deletions, etc., that occur in gene enhancers, exons, introns, promoters, 5' UTR, 3'UTR, etc.

As used herein "rs1110470" refers to a C/T (reverse strand) SNP located within an intron of the human IL-4RA gene (IL-4Rα; IL-4 receptor alpha) (GeneBank Accession No. NM_000418.3). The rs1110470 polymorphic site is located at chromosomal position 27336427 (build 138; assembly GRCh37.p10), which is position 27276427 of Contig NT_010393.16.

As used herein "rs3024530" refers to an A/G (forward strand) SNP located within an intron of IL-4RA gene (GeneBank Accession No. NM_000418.3). The rs3024530 polymorphic site is located at chromosomal position 27350687 (build 138; assembly GRCh37.p10), which is position 27290687 of Contig NT_010393.16.

As used herein "rs1805010" refers to an A/G (forward strand) SNP located within an exon of IL-4RA gene (GeneBank Accession No. NM_000418.3), and encoding an Ile to Val change. The rs1805010 polymorphic site is located at chromosomal position 27356203 (build 138; assembly GRCh37.p10), which is position 27296203 of Contig NT_010393.16.

As used herein "rs2239347" refers to an G/T (reverse strand) SNP located within an intron of IL-4RA gene (GeneBank Accession No. NM_000418.3). The rs2239347 polymorphic site is located at chromosomal position 27359021 (build 138; assembly GRCh37.p10), which is position 27299021 of Contig NT_010393.16.

As used herein "rs1805011" refers to an A/C (forward strand) SNP located within an exon of IL-4RA gene (GeneBank Accession No. NM_000418.3), and encoding an Glu to Ala change. The rs1805011 polymorphic site is located at chromosomal position 27373872 (build 138; assembly GRCh37.p10), which is position 27313872 of Contig NT_010393.16.

As used herein "rs1801275" refers to an A/G (forward strand) SNP located within an exon of IL-4RA gene (GeneBank Accession No. NM_000418.3), and encoding an Gln to Arg change. The rs1801275 polymorphic site is located at chromosomal position 27374400 (build 138; assembly GRCh37.p10), which is position 27314400 of Contig NT_010393.16.

As used herein "rs8832" refers to an A/G (forward strand) SNP located within the 3' UTR (untranslated) region of IL-4RA gene (GeneBank Accession No. NM_000418.3). The rs8832 polymorphic site is located at chromosomal position 27375787 (build 138; assembly GRCh37.p10), which is position 27315787 of Contig NT_010393.16.

As used herein "rs1029489" refers to an C/T (reverse strand) SNP located 3' proximal of IL-4RA gene (GeneBank Accession No. NM_000418.3). The rs1029489 polymorphic site is located at chromosomal position 27376217 (build 138; assembly GRCh37.p10), which is position 27316217 of Contig NT_010393.16.

As used herein "rs4787956" refers to an A/G (forward strand) SNP located 3' proximal of IL-4RA gene (GeneBank Accession No. NM_000418.3). The rs4787956 polymorphic site is located at chromosomal position 27378249 (build 138; assembly GRCh37.p10), which is position 27318249 of Contig NT_010393.16.

As recognized by the skilled artisan, nucleic acid samples containing a particular SNP may be complementary double stranded molecules and thus reference to a particular site on the sense strand refers as well to the corresponding site on the complementary antisense strand. Similarly, reference to a particular genotype obtained for a SNP on both copies of one strand of a chromosome is equivalent to the complementary genotype obtained for the same SNP on both copies of the other strand.

As used herein, "genomic sequence" refers to a DNA sequence present in a genome, and includes a region within an allele, an allele itself, or a larger DNA sequence of a chromosome containing an allele of interest.

Products of the AIR markers of the invention can include nucleic acid products and polypeptide products. "Polypeptide product" refers to a polypeptide including the amino acid encoded by an AIR marker and fragments thereof. "Nucleic acid product" refers to any DNA (e.g., genomic, cDNA, etc.) or RNA (e.g., pre-mRNA, mRNA, miRNA, etc.) products of an AIR markers and fragments thereof.

An "equivalent genetic marker" refers to a genetic marker that is correlated to an allele of interest, e.g., it displays linkage disequilibrium (LD) or is in genetic linkage with the allele of interest. Equivalent genetic markers may be used to determine if a patient has an AIR marker, rather than directly interrogating a biological sample from the patient for the allele per se. Various programs exist to help determine LD for particular SNPs, e.g, HaploBlock (available at bioinfo.cs.technion.ac.il/haploblock/), HapMap, WGA Viewer.

The term "probe" refers to any composition of matter that is useful for specifically detecting another substance, e.g., a substance related to an AIR marker. A probe can be an oligonucleotide (including a conjugated oligonucleotide) that specifically hybridizes to a genomic sequence of an AIR marker, or a nucleic acid product of an AIR marker. A conjugated oligonucleotide refers to an oligonucleotide covalently bound to chromophore or molecules containing a ligand (e.g., an antigen), which is highly specific to a receptor molecule (e.g., an antibody specific to the antigen). The probe can also be a PCR primer, e.g., together with another primer, for amplifying a particular region within an AIR marker. Further, the probe can be an antibody that specifically binds to polypeptide products of these alleles. Further, the probe can be any composition of matter capable of detecting (e.g., binding or hybridizing) an equivalent genetic marker of an AIR marker. In preferred embodiments, the probe specifically hybridizes to a nucleic acid sequence (preferably genomic DNA) or specifically binds to a polypeptide sequence of an allele of interest.

The phrase "specifically hybridizes" is used to refer to hybridization under stringent hybridization conditions. Stringent conditions are known to those skilled in the art and can be found in Current Protocols in Molecular Biology, John Wiley & Sons, N.Y. (1989), 6.3.1-6.3.6. Aqueous and non-aqueous methods are described in that reference and either can be used. One example of stringent hybridization conditions is hybridization in 6× sodium chloride/sodium citrate (SSC) at about 45° C., followed by at least one wash in 0.2×SSC, 0.1% SDS at 50° C. A second example of stringent hybridization conditions is hybridization in 6×SSC at about 45° C., followed by at least one wash in 0.2×SSC, 0.1% SDS at 55° C. Another example of stringent hybridization conditions is hybridization in 6×SSC at about 45° C., followed by at least one wash in 0.2×SSC, 0.1% SDS at 60° C. A further example of stringent hybridization conditions is hybridization in 6×SSC at about 45° C., followed by at least one wash in 0.2×SSC, 0.1% SDS at 65° C. High stringent conditions include hybridization in 0.5 M sodium phosphate, 7% SDS at 65° C., followed by at least one wash at 0.2×SSC, 1% SDS at 65° C.

The phrase "a region of a nucleic acid" is used to indicate a smaller sequence within a larger sequence of nucleic acids. For example, a gene is a region of a chromosome, an exon is a region of a gene, etc.

The term "specifically binds" in the context of polypeptides is used to mean that a probe binds a given polypeptide target (e.g., a polypeptide product an AIR marker) rather than randomly binding undesirable polypeptides. However, "specifically binds" does not exclude some cross reactivity with undesirable polypeptides, as long as that cross reactivity does not interfere with the capability of the probe to provide a useful measure of the presence of the given polypeptide target.

The term "capable" is used to mean that ability to achieve a given result, e.g., a probe that is capable of detecting the presence of a particular substance means that the probe may be used to detect the particular substance.

An "oliogonucelotide" refers to a short sequence of nucleotides, e.g., 2-100 bases.

The term "biological sample" as used herein refers to a sample from a patient, which may be used for the purpose of identification, diagnosis, prediction, or monitoring. Preferred samples include synovial fluid, blood, blood-derived product (such as buffy coat, serum, and plasma), lymph, urine, tear, saliva, hair bulb cells, cerebrospinal fluid, buccal swabs, feces, synovial fluid, synovial cells, sputum, or tissue samples (e.g., cartilage samples). In addition, one of skill in the art would realize that some samples would be more readily analyzed following a fractionation or purification procedure, for example, isolation of DNA from whole blood.

The term "IL-13" includes wild-type IL-13 from various species (e.g., human, mouse, and monkey), polymorphic variants of IL-13, and functional equivalents of IL-13. Functional equivalents of IL-13 according to the present disclosure preferably have at least about 85%, 95%, 96%, 97%, 98%, or even 99% overall sequence identity with the wild-type IL-13 (e.g., human IL-13). More particularly, IL-13 refers to the polypeptide sequence set forth as in the following paragraph.

The IL-13 polypeptide has the below sequence. The N-terminal 34 amino acid residues (in italics) is a signal peptide. The mature cytokine thus has 112 amino acid residues. Anti-IL-13 antibodies will bind to an epitope on the mature polypeptide.

Interleukin 13 amino acid sequence:

(SEQ ID No. 1)

```
  1  MHPLLNPLLL ALGLMALLLT TVIALTCLGG FASPGPVPPS TALRELIEEL VNITQNQKAP

61  LCNGSMVWSI NLTAGMYCAA LESLINVSGC SAIEKTQRML SGFCPHKVSA GQFSSLHVRD

121  TKIEVAQFVK DLLLEILKKLF REGRFN
```

As also further set forth in detail in the EXAMPLES, in particular embodiments of the inventive methods, the IL-13 antagonist utilized in the methods, including antibody 01951/G12 binds an epitope that includes the residues: FCPHKV (SEQ ID NO: 67) (underlined as residues 103-107 of SEQ ID NO.1).

IL-13 Antagonists

In principle any anti-IL-13 antagonists, including antibodies, which inhibit or neutralize the activity of IL-13 may be used in the invention, so long as the anti-IL-13 antagonist or antibody determinably and selectively reduces exacerbations in an asthma patient that is positive for at least one AIR marker selected from said group consisting of AIR marker—1, 2, 3, 4, 5, 6, 7, 8, and 9 as set forth in the methods of the invention. Such antibodies can be selected among those known in the art, see for example in WO2005/007699, U.S. Pat. No. 6,468,528, WO03007685, WO03034984, US20030143199, US2004028650, US20040242841, US2004023337, US20040248260, US20050054055, US20050065327, WO2006/124451, WO2006/003407, WO2005/062967, WO2006/085938, WO2006/055638, WO2007/036745, WO2007/080174 or WO2007/085815 Such antibodies are known in the art, see for example in WO2005/007699, US6468528, WO03007685, WO03034984, US20030143199, US2004028650, US20040242841, US2004023337, US20040248260, US20050054055, US20050065327, WO2006/124451, WO2006/003407, WO2005/062967, WO2006/085938, WO2006/055638, WO2007/036745, WO2007/080174 or WO2007/085815, WO2012/049278, and WO2008/106116.

In one embodiment, the antibodies used in the methods of the invention comprise one or more of the following CDRs. The CDRs listed in table 2a and 3a were determined according to the Kabat definition (E. Kabat et al, 1991, Sequences of Proteins of immunological Interest, 5$^{th}$ edition, public health Service, HIH, Bethesda, Md.:

TABLE 2

| Antibody | HCDR1 | SEQ ID No. HCDR1 | HCDR2 | SEQ ID No. HCDR2 | HCDR3 | SEQ ID No. HCDR3 |
| --- | --- | --- | --- | --- | --- | --- |
| 01951/G12 | GFTFSSYG | 2 | IWYDGSN | 3 | ARLWFGDLD | 4 |

TABLE 2a

| Antibody | HCDR1 | SEQ ID No. HCDR1 | HCDR2 | SEQ ID No. HCDR2 | HCDR3 | SEQ ID No. HCDR3 |
| --- | --- | --- | --- | --- | --- | --- |
| 01951/G12 | SYGMH | 5 | IIWYDGSNKYYADSVKG | 6 | LWFGDLDAFDI | 7 |

TABLE 3

| Antibody | LCDR1 | SEQ ID No. LCDR1 | LCDR2 | SEQ ID No. LCDR2 | LCDR3 | SEQ ID No. LCDR3 |
| --- | --- | --- | --- | --- | --- | --- |
| 01951/G12 | QSVSSY | 8 | DA | 9 | QQRSSWPPV | 10 |

TABLE 3a

| Antibody | LCDR1 | SEQ ID No. LCDR1 | LCDR2 | SEQ ID No. LCDR2 | LCDR3 | SEQ ID No. LCDR3 |
| --- | --- | --- | --- | --- | --- | --- |
| 01951/G12 | RAGQSVSSYLV | 11 | DASNRAT | 12 | QQRSSWPPVYT | 13 |

The full IgG1 antibody light and heavy chain constant regions are also shown below, incorporating, as an example, the variable regions of antibody 01951/G12 (emboldened).

01951/G12 Antibody Sequence (i) HC Variable Region

The HC variable amino acid sequence for 01951/G12 is shown in SEQ ID NO: 14 and is encoded by the nucleotide sequence shown in SEQ ID NO: 15

```
E   V   Q   L   V   E   S   G   G   G   V   V   Q   P   G   R   S   L   R   L
gaagtgcagctggtggagtctgggggaggcgtggtccagcctgggaggtccctgagactc    60

S   C   A   A   S   G   F   T   F   S   S   Y   G   M   H   W   V   R   Q   A
tcctgtgcagcgtctggattcaccttcagtagctatggcatgcactgggtccgccaggct    120
```

```
           P  G  K  G  L  E  W  V  A  I  I  W  Y  D  G  S  N  K  Y  Y
           ccaggcaaggggctggagtgggtggcaattatatggtatgatggaagtaataaatactat  180

A  D  S  V  K  G  R  F  T  I  S  R  D  N  S  K  N  T  L  Y
           gcggactccgtgaagggccgattcaccatctccagagacaattccaagaacacgctgtat  240

L  Q  M  N  S  L  R  A  E  D  T  A  V  Y  Y  C  A  R  L  W
           ctgcaaatgaacagcctgagagccgaggacacggctgtgtattactgtgcgaggctatgg  300

F  G  D  L  D  A  F  D  I  W  G  Q  G  T  M  V  T              (SEQ ID NO: 14)
           ttcggggacttagatgcttttgatatctggggccaagggacaatggtcacc          351 (SEQ ID NO: 15)
```

(ii) LC Variable Region
  The LC variable amino acid sequence for 01951/G12 is shown in SEQ ID NO: 16 and is encoded by the nucleotide sequence shown in SEQ ID NO: 17

```
           E  I  V  L  T  S  P  A  T  T  L  S  L  S  P  G  E  R  A  I
           gaaattgtgttgacgcagtctccagccaccctgtctttgtctccaggggaaagagccatc   60

L  S  C  R  A  G  Q  S  V  S  S  Y  L  V  W  Y  Q  Q  K  P
           ctctcctgcagggccggtcagagtgttagcagttacttagtctggtaccaacagaaacct  120

G  Q  A  P  R  R  L  L  I  Y  D  A  R  A  T  T  G  I  P  A
           ggccaggctcccaggctcctcatctatgatgcatccaacagggccactggcatcccagcc  180

R  F  S  G  S  G  S  G  T  D  F  T  L  T  I  S  S  L  E  P
           aggttcagtggcagtgggtctgggacagacttcactctcaccatcagcagcctagagcct  240

E  D  F  A  V  Y  Y  C  Q  Q  R  S  S  W  P  P  V  Y  T  F
           gaagattttgcagtttattactgtcagcagcgcagcagctggcctccggtgtacactttt  300

G  Q  G  T                                                      (SEQ ID NO: 16)
           ggccaggggacc                                                 312 (SEQ ID NO: 17)
```

Full Antibody IgG1 Light Chain Sequence Incorporating the Variable Region of Antibody 01951/G12 (Emboldened)
  The LC amino acid sequence is shown in SEQ ID NO: 18 and is encoded by the nucleotide sequence of SEQ ID NO: 19

```
          M     S     V     L     T     Q     V     L     A     L     L     L     W     L     T     G
   1    ATGAGTGTGC TCACTCAGGT CCTGGCGTTG CTGCTGCTGT GGCTTACAGG

T     R     C     E     I     V     L     T     Q     S     P     A     T     L     S     L     S
  51    TACGCGTTGT GAAATTGTGT TGACGCAGTC TCCAGCCACC CTGTCTTTGT

P     G     E     R     A     I     L     S     C     R     A     G     Q     S     V     S
 101    CTCCAGGGGA AAGAGCCATC CTCTCCTGCA GGGCCGGTCA GAGTGTTAGC

S     Y     L     V     W     Y     Q     K     P     G     Q     A     P     R     L     L
 151    AGTTACTTAG TCTGGTACCA ACAGAAACCT GGCCAGGCTC CCAGGCTCCT

I     Y     D     A     S     N     R     A     T     G     I     P     A     R     F     S     G
 201    CATCTATGAT GCATCCAACA GGGCCACTGG CATCCCAGCC AGGTTCAGTG

S     G     S     G     T     D     F     T     L     T     I     S     S     L     E     P
 251    GCAGTGGGTC TGGGACAGAC TTCACTCTCA CCATCAGCAG CCTAGAGCCT

E     D     F     A     V     Y     Y     C     Q     Q     R     S     S     W     P     P     V
 301    GAAGATTTTG CAGTTTATTA CTGTCAGCAG CGCAGCAGCT GGCCTCCGGT

Y     T     F     G     Q     G     T     K     L     E     I     K     R     T     V     A     A
 351    GTACACTTTT GGCCAGGGGA CCAAGCTTGA AATCAAACGA ACTGTGGCTG

P     S     V     F     I     F     P     P     S     D     E     Q     L     K     S     G
 401    CACCATCTGT CTTCATCTTC CCGCCATCTG ATGAGCAGTT GAAATCTGGA

T     A     S     V     V     C     L     N     N     F     Y     P     R     E     A     K
 451    ACTGCCTCTG TTGTGTGCCT GCTGAATAAC TTCTATCCCA GAGAGGCCAA

V     Q     W     K     V     D     N     A     L     Q     S     G     N     S     Q     E     S
 501    AGTACAGTGG AAGGTGGATA ACGCCCTCCA ATCGGGTAAC TCCCAGGAGA
```

```
            V  T  E     Q  D  S     K  D  S  T     Y  S  L     S  S  T
551  GTGTCACAGA GCAGGACAGC AAGGACAGCA CCTACAGCCT CAGCAGCACC

L  T  L  S     K  A  D     Y  E  K     H  K  V  Y     A  C  E
601  CTGACGCTGA GCAAAGCAGA CTACGAGAAA CACAAAGTCT ACGCCTGCGA

V  T  H     Q  G  L  S     S  P  V     T  K  S     F  N  R  G
651  AGTCACCCAT CAGGGCCTGA GCTCGCCCGT CACAAAGAGC TTCAACAGGG

E  C  *       (SEQ ID NO: 18)
701  GAGAGTGTTA G  (SEQ ID NO: 19)
```

Full Antibody IgG1 Heavy Chain Sequence Incorporating the Variable Region of Antibody 01951/G12 (Emboldened)

The HC amino acid sequence is shown in SEQ ID NO: 20 and is encoded by the nucleotide sequence of SEQ ID NO: 21

```
        M  A  W  V     W  T  L     P  F  L     M  A  A  A     Q  S  V
  1  ATGGCTTGGG TGTGGACCTT GCCATTCCTG ATGGCAGCTG CCCAAAGTGT

Q  A  E     V  Q  L  V     E  S  G     G  G  V     Q  P  G
 51  CCAGGCAGAA GTGCAGCTGG TGGAGTCTGG GGGAGGCGTG GTCCAGCCTG

R  S  L     R  L  S     C  A  A  S     G  F  T     F  S  S
101  GGAGGTCCCT GAGACTCTCC TGTGCAGCGT CTGGATTCAC CTTCAGTAGC

Y  G  M  H     W  V  R     Q  A  P     G  K  G  L     E  W  V
151  TATGGCATGC ACTGGGTCCG CCAGGCTCCA GGCAAGGGGC TGGAGTGGGT

A  I  I     W  Y  D  G     S  N  K     Y  Y  A     D  S  V  K
201  GGCAATTATA TGGTATGATG GAAGTAATAA ATACTATGCG GACTCCGTGA

G  R  F     T  I  S     R  D  N  S     K  N  T     L  Y  L
251  AGGGCCGATT CACCATCTCC AGAGACAATT CCAAGAACAC GCTGTATCTG

Q  M  N  S     L  R  A     E  D  T     A  V  Y  Y     C  A  R
301  CAAATGAACA GCCTGAGAGC CGAGGACACG GCTGTGTATT ACTGTGCGAG

L  W  F     G  D  L  D     A  F  D     I  W  G     Q  G  T  M
351  GCTATGGTTC GGGGACTTAG ATGCTTTTGA TATCTGGGGC CAAGGGACAA

V  T  V     S  S  A     S  T  K  G     P  S  V     F  P  L
401  TGGTCACCGT CTCCTCAGCC TCCACCAAGG GCCCATCGGT CTTCCCCCTG

A  P  S  S     K  S  T     S  G  G     T  A  A  L     G  C  L
451  GCACCCTCCT CCAAGAGCAC CTCTGGGGGC ACAGCGGCCC TGGGCTGCCT

V  K  D     Y  F  P  E     P  V  T     V  S  W     N  S  G  A
501  GGTCAAGGAC TACTTCCCCG AACCGGTGAC GGTGTCGTGG AACTCAGGCG

L  T  S     G  V  H     T  F  P  A     V  L  Q     S  S  G
551  CCCTGACCAG CGGCGTGCAC ACCTTCCCGG CTGTCCTACA GTCCTCAGGA

L  Y  S  L     S  S  V     V  T  V     P  S  S  S     L  G  T
601  CTCTACTCCC TCAGCAGCGT CGTGACCGTG CCCTCCAGCA GCTTGGGCAC

Q  T  Y     I  C  N  V     N  H  K     P  S  N     T  K  V  D
651  CCAGACCTAC ATCTGCAACG TGAATCACAA GCCCAGCAAC ACCAAGGTGG

K  R  V     E  P  K     S  C  D  K     T  H  T     C  P  P
701  ACAAGAGAGT TGAGCCCAAA TCTTGTGACA AAACTCACAC ATGCCCACCG

C  P  A  P     E  L  L     G  G  P     S  V  F  L     F  P  P
751  TGCCCAGCAC CTGAACTCCT GGGGGGACCG TCAGTCTTCC TCTTCCCCCC

K  P  K     D  T  L  M     I  S  R     T  P  E     V  T  C  V
801  AAAACCCAAG GACACCCTCA TGATCTCCCG GACCCCTGAG GTCACATGCG

V  V  D     V  S  H     E  D  P  E     V  K  F     N  W  Y
851  TGGTGGTGGA CGTGAGCCAC GAAGACCCTG AGGTCAAGTT CAACTGGTAC

V  D  G  V     E  V  H     N  A  K     T  K  P  R     E  E  Q
901  GTGGACGGCG TGGAGGTGCA TAATGCCAAG ACAAAGCCGC GGGAGGAGCA

Y  N  S     T  Y  R  V     V  S  V     L  T  V     L  H  Q  D
951  GTACAACAGC ACGTACCGTG TGGTCAGCGT CCTCACCGTC CTGCACCAGG
```

```
            W   L   N     G   K   E     Y   K   C   K     V   S   N     K   A   L
1001        ACTGGCTGAA    TGGCAAGGAG    TACAAGTGCA    AGGTCTCCAA    CAAAGCCCTC

P   A   P   I     E   K   T     I   S   K     A   K   G   Q     P   R   E
1051        CCAGCCCCCA    TCGAGAAAAC    CATCTCCAAA    GCCAAAGGGC    AGCCCCGAGA

P   Q   V     Y   T   L   P     P   S   R     E   E   M     T   K   N   Q
1101        ACCACAGGTG    TACACCCTGC    CCCCATCCCG    GGAGGAGATG    ACCAAGAACC

V   S   L     T   C   L     V   K   G   F     Y   P   S     D   I   A
1151        AGGTCAGCCT    GACCTGCCTG    GTCAAAGGCT    TCTATCCCAG    CGACATCGCC

V   E   W   E     S   N   G     Q   P   E     N   N   Y   K     T   T   P
1201        GTGGAGTGGG    AGAGCAATGG    GCAGCCGGAG    AACAACTACA    AGACCACGCC

P   V   L     D   S   D   G     S   F   F     L   Y   S     K   L   T   V
1251        TCCCGTGCTG    GACTCCGACG    GCTCCTTCTT    CCTCTATAGC    AAGCTCACCG

D   K   S     R   W   Q     Q   G   N   V     F   S   C     S   V   M
1301        TGGACAAGAG    CAGGTGGCAG    CAGGGGAACG    TCTTCTCATG    CTCCGTGATG

H   E   A   L     H   N   H     Y   T   Q     K   S   L   S     L   S   P
1351        CATGAGGCTC    TGCACAACCA    CTACACGCAG    AAGAGCCTCT    CCCTGTCCCC

G   K   *       (SEQ ID NO: 20)
1401        GGGTAAATGA      (SEQ ID NO: 21)
```

In various embodiments, the invention encompasses disclosed pharmaceutical compositions, regimens, processes, uses, methods and kits utilizing an IL-13 antagonist (e.g., an anti-IL-13 antibody or antigen-binding portion thereof) set forth herein. In particular embodiments the kits comprise nucleic acid probes for detecting an AIR marker set forth herein. In further embodiments, the kits further comprise instructions comprising diagnosis or treatment of asthma.

In a particular embodiment, the invention provides a kit for determining the presence of at least one AIR marker selected from the group consisting of AIR marker 1, 2, 3, 4, 5, 6, 7, 8, or 9 in a sample obtained from an asthma patient, the kit comprising: a container containing one or more probes that specifically hybridize under stringent conditions to a nucleic acid comprising the responsive allele in one or more SNPs selected from the group set forth in Table 1.

In another embodiment, the kit comprises instructional materials indicating that the presence of at least AIR marker in a nucleic acid sample from the patient indicates that the patient is a candidate for treatment with an IL-13 antagonist as set forth herein.

In another embodiment, the kit comprises instructional materials indicating that the presence of at least 2 AIR markers in a nucleic acid sample from the patient indicates that the patient is a candidate for treatment with an IL-13 antagonist as set forth herein.

In another embodiment, the kit comprises instructional materials indicating that the presence of at least 3, 4, 5, 6, 7, 8, or 9 AIR markers in a nucleic acid sample from the patient indicates that the patient is a candidate for treatment with an IL-13 antagonist as set forth herein.

In another embodiment, the kit comprises a container containing one or more probes that specifically hybridize under stringent conditions to a nucleic acid comprising the responsive allele in one or more SNPs selected from the group set forth in Table 1. In another, the nucleic acid comprises two or more SNPs selected from the group set forth in Table 1. In another, the nucleic acid comprises 2, 3, 3, 4, 5, 6, 7, 8, or 9 or more SNPs selected from the group set forth in Table 1.

In another embodiment, the one or more probes specifically hybridize under stringent conditions to a nucleic acid comprising the responsive allele in SNP rs 8832, and/or rs 1050.

In another, the one or more probes and/or primers comprise probes and/or primers for use in nucleic acid amplification reaction.

Techniques for Assaying, Diagnostic Methods and Methods of Producing a Transmittable Form of Information The disclosed methods are useful for the treatment, prevention, or amelioration of asthma diseases, as well as predicting the likelihood of an asthma patient's response to treatment with an IL-13 antagonist. These methods employ, inter alia, determining whether a patient has an AIR marker in a sample from the patient.

A biological sample from the patient may be assayed for the presence of an AIR marker by any applicable conventional means, which will be selected depending on whether the particular marker falls within an exon, an intron, a non-coding portion of mRNA or a non-coding genomic sequence.

Numerous biological samples may be used to identify the presence of alleles or proteins, the level of expression of genes or proteins, and the activity of a protein, e.g., blood, synovial fluid, buffy coat, serum, plasma, lymph, feces, urine, tear, saliva, cerebrospinal fluid, buccal swabs, sputum, or tissue. Various sources within a biological sample may be used in the disclosed methods, e.g., one may assay genomic DNA obtained from a biological sample to detect an AIR marker, or one may assay products of a an AIR marker, e.g., nucleic acid products (e.g., DNA, pre-mRNA, mRNA, micro RNAs, etc.) and polypeptide products (e.g., expressed proteins) obtained from a biological sample.

The inventive discovery encompasses the determination that the various AIR markers of Table 1 are useful for predicting certain patient's response to treatment by IL-13 antagonism. Of the SNPs in Table 1, most are found in genomic DNA and introns, such that a patient's allelic status may be determined by interrogating, e.g., pre-mRNA or genomic DNA. However, the presence of the AIR markers corresponding to exonic locations may be determined by assaying genomic DNA, RNA and/or protein sequence. Accordingly, a skilled artisan will understand that one may identify whether a subject has a given AIR marker by assaying a nucleic acid product of an AIR marker, a polypeptide product of an AIR marker, or an equivalent genetic marker of an AIR marker, as appropriate. In preferred embodiments, a genomic sequence of an AIR marker is analyzed to determine whether a subject has an AIR marker.

Numerous methods and devices are available to identify the presence of an AIR marker or polymorphism that results in a decreased level of expression, level of the coded protein or level of the protein's activity. DNA (genomic and cDNA) for SNP detection can be prepared from a biological sample by methods well known in the art, e.g., phenol/chloroform extraction, PUREGENE DNA® purification system from GentAS Systems (Qiagen, Calif.). Detection of a DNA sequence may include examining the nucleotide(s) located at either the sense or the antisense strand within that region. The presence of polymorphisms in a patient may be detected from DNA (genomic or cDNA) obtained from PCR using sequence-specific probes, e.g., hydrolysis probes from Taqman, Beacons, Scorpions; or hybridization probes that detect the marker or polymorphism. For the detection of the polymorphism, sequence specific probes may be designed such that they specifically hybridize to the genomic DNA for the alleles of interest or, in some cases, an RNA of interest. Primers and probes for polymorphic sites (e.g., SNP) may be designed based on context sequences found in the NCBI SNP database available at: www.ncbi.nlm.nih.gov/snp. These probes may be labeled for direct detection or contacted by a second, detectable molecule that specifically binds to the probe. The PCR products also can be detected by DNA-binding agents. Said PCR products can then be subsequently sequenced by any DNA sequencing method available in the art. Alternatively the presence of allele can be detected by sequencing using any sequencing methods such as, but not limited to, Sanger-based sequencing, pyrosequencing or next generation sequencing (Shendure J. and Ji, H., Nature Biotechnology (1998), Vol. 26, Nr 10, pages 1135-1145). Optimised allelic discrimination assays for SNPs may be purchased from Applied Biosystems (Foster City, Calif., USA).

Various techniques can be applied to interrogate a particular polymorphism (e.g., SNP), including, e.g., hybridization-based methods, such as dynamic allele-specific hybridization (DASH) genotyping, polymorphic site (e.g., SNP) detection through molecular beacons (Abravaya K., et al. (2003) Clin Chem Lab Med. 41:468-474), Luminex xMAP Technology®, Illumina Golden Gate® technology and commercially available high-density oligonucleotide SNP arrays (e.g., the Affymetrix Human SNP 5.0 GeneChip® performs a genome-wide assay that can genotype over 500,000 human SNPs), BeadChip® kits from Illumina, e.g, Human660W-Quad and Human 1.2M-Duo); enzyme-based methods, such as restriction fragment length polymorphism (RFLP), PCR-based methods (e.g., Tetraprimer ARMS-PCR), Invader assays (Olivier M. (2005) Mutat Res. 573(1-2):103-10), various primer extension assays (incorporated into detection formats, e.g., MALDI-TOF Mass spectrometry, electrophoresis, blotting, and ELISA-like methods), TaqMan® assays, and oligonucleotide ligase assays; and other post-amplification methods, e.g., analysis of single strand conformation polymorphism (Costabile et al. (2006) Hum. Mutat. 27(12):1163-73), temperature gradient gel electrophoresis (TGGE), denaturing high performance liquid chromatography, high-resolution melting analysis, DNA mismatch-binding protein assays (e.g., MutS protein from *Thermus aquaticus* binds different single nucleotide mismatches with different affinities and can be used in capillary electrophoresis to differentiate all six sets of mismatches), SNPLex® (proprietary SNP detecting system available from Applied Biosystems), capillary electrophoresis, mass spectrometry, and various sequencing methods, e.g., pyrosequencing and next generation sequencing, etc. Commercial kits for SNP genotyping include, e.g., Fluidigm Dynamic Array® IFCs (Fluidigm), TaqMan® SNP Genotyping Assay (Applied Biosystems), MassARRAY® iPLEX Gold (Sequenom), Type-it Fast® SNP Probe PCR Kit (Quiagen), etc.

In some embodiments, the presence of a polymorphic site (e.g., SNP) in a patient is detected using a hybridization assay. In a hybridization assay, the presence of the genetic marker is determined based on the ability of the nucleic acid from the sample to hybridize to a complementary nucleic acid molecule, e.g., an oligonucleotide probe. A variety of hybridization assays are available. In some, hybridization of a probe to the sequence of interest is detected directly by visualizing a bound probe, e.g., a Northern or Southern assay. In these assays, DNA (Southern) or RNA (Northern) is isolated. The DNA or RNA is then cleaved with a series of restriction enzymes that cleave infrequently in the genome and not near any of the markers being assayed. The DNA or RNA is then separated, e.g., on an agarose gel, and transferred to a membrane. A labeled probe or probes, e.g., by incorporating a radionucleotide or binding agent (e.g., SYBR® Green), is allowed to contact the membrane under low-, medium- or high-stringency conditions. Unbound probe is removed and the presence of binding is detected by visualizing the labeled probe. In some embodiments, arrays, e.g., the MassARRAY® system (Sequenom, San Diego, Calif., USA) may be used to genotype a subject.

Traditional genotyping methods may also be modified for use in genotyping. Such traditional methods include, e.g., DNA amplification techniques such as PCR and variants thereof, direct sequencing, SSO hybridization coupled with the Luminex xMAP® technology, SSP typing, and SBT.

Sequence-Specific Oligonucleotide (SSO) typing uses PCR target amplification, hybridization of PCR products to a panel of immobilized sequence-specific oligonucleotides on the beads, detection of probe-bound amplified product by color formation followed by data analysis. Those skilled in the art would understand that the described Sequence-Specific Oligonucleotide (SSO) hybridization may be performed using various commercially available kits, such as those provided by One Lambda, Inc. (Canoga Park, Calif.) or Lifecodes HLA Typing Kits (Tepnel Life Sciences Corp.) coupled with Luminex® technology (Luminex, Corporation, TX). LABType® SSO is a reverse SSO (rSSO) DNA typing solution that uses sequence-specific oligonucleotide (SSO) probes and color-coded microspheres to identify HLA alleles. The target DNA is amplified by polymerase chain reactions (PCR) and then hybridized with the bead probe array. The assay takes place in a single well of a 96-well PCR plate; thus, 96 samples can be processed at one time.

Sequence Specific Primers (SSP) typing is a PCR based technique which uses sequence specific primers for DNA based typing. The SSP method is based on the principle that only primers with completely matched sequences to the target sequences result in amplified products under controlled PCR conditions. Allele sequence-specific primer pairs are designed to selectively amplify target sequences which are specific to a single allele or group of alleles. PCR products can be visualized on agarose gel. Control primer pairs that matches non-allelic sequences present in all samples act as an internal PCR control to verify the efficiency of the PCR amplification. Those skilled in the art would understand that low, medium and high resolution genotyping with the described sequence-specific primer typing may be performed using various commercially available kits, such as the Olerup SSP™ kits (Olerup, Pa.) or (Invitrogen) or Allset and ™Gold DQA1 Low resolution SSP (Invitrogen).

Sequence Based Typing (SBT) is based on PCR target amplification, followed by sequencing of the PCR products and data analysis.

In some cases, RNA, e.g., mature mRNA, pre-mRNA, can also be used to determine the presence of particular polymorphisms (see Table 1). Analysis of the sequence of mRNA transcribed from a given gene can be performed using any known method in the art including, but not limited, to Northern blot analysis, nuclease protection assays (NPA), in situ hybridization, reverse transcription-polymerase chain reaction (RT-PCR), RT-PCR ELISA, TaqMan-based quantitative RT-PCR (probe-based quantitative RT-PCR) and SYBR green-based quantitative RT-PCR. In one example, detection of mRNA levels involves contacting the isolated mRNA with an oligonucleotide that can hybridize to mRNA encoded by an AIR marker. The nucleic acid probe can typically be, for example, a full-length cDNA, or a portion thereof, such as an oligonucleotide of at least 7, 15, 30, 50, or 100 nucleotides in length and sufficient to specifically hybridize under stringent conditions to the mRNA. Hybridization of an mRNA with the probe indicates that the marker in question is being expressed. In one format, the RNA is immobilized on a solid surface and contacted with a probe, for example by running the isolated RNA on an agarose gel and transferring the mRNA from the gel to a membrane, such as nitrocellulose. Amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers. PCR products can be detected by any suitable method including, but not limited to, gel electrophoresis and staining with a DNA-specific stain or hybridization to a labeled probe.

The level of expression of a gene may be determined by measuring RNA (or reverse transcribed cDNA) levels using various techniques, e.g., a PCR-based assay, reverse-transcriptase PCR (RT-PCR) assay, Northern blot, etc. Quantitative RT-PCR with standardized mixtures of competitive templates can also be utilized.

In some cases, the presence of a polymorphism in a patient can be determined by analyzing polypeptide products of the AIR markers (see Table 1). Detection of polypeptide products can be performed using any known method in the art including, but not limited to, immunocytochemical staining, ELISA, flow cytometry, Western blot, spectrophotometry, HPLC, and mass spectrometry.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and then processed quickly through washes and detection steps to generate a measurable signal, such as a colored spot.

In a two-step assay, immobilized polypeptide products of an AIR marker or ERAP1 protein may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art. The antibodies may be labeled with a radioactive atom, an enzyme, a chromophoric or fluorescent moiety, or a colorimetric tag. The choice of tagging label also will depend on the detection limitations desired. Enzyme assays (ELISAs) typically allow detection of a colored product formed by interaction of the enzyme-tagged complex with an enzyme substrate. Some examples of radioactive atoms include $^{32}P$, $^{125}I$, $^{3}H$, and $^{14}P$. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

In one aspect, the present disclosure contemplates the use of a sandwich technique for detecting polypeptide products in biological samples. The technique requires two antibodies capable of binding the protein of interest: e.g., one immobilized onto a solid support and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing polypeptide products are placed in this system, the polypeptide products binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Preferably, the presence of polypeptide products in a sample is detected by radioimmunoassays or enzyme-linked immunoassays, competitive binding enzyme-linked immunoassays, dot blot, Western blot, chromatography, preferably high performance liquid chromatography (HPLC), or other assays known in the art. Specific immunological binding of the antibody to the protein or polypeptide can be detected directly or indirectly.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory).

In Western blot, the sample is separated by SDS-PAGE. The gel is transferred to a membrane. The membrane is incubated with labeled antibody for detection of the desired protein.

The assays described above involve steps such as but not limited to, immunoblotting, immunodiffusion, immunoelectrophoresis, or immunoprecipitation. In some embodiments, an automatic analyzer is used to determine the presence of an AIR marker.

In performing any of the methods described herein that require determining the presence of an AIR marker or polymorphism, such determination may be made by consulting a data repository that contains sufficient information on the patient's genetic composition to determine whether the patient has the marker of interest. Preferably, the data repository lists the genotype present (or absent) in the individual. The data repository could include the individual's patient records, a medical data card, a file (e. g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a smart phone, Palm Pilot, a tape recorder, a zip disk, the computer's internal ROM (read-only-memory) or the internet or worldwide web. Other media for the storage of files accessible by a computer will be obvious to one skilled in the art.

Typically, once the presence of an AIR marker or polymorphism is determined, physicians or genetic counselors or patients or other researchers may be informed of the result. Specifically the result can be cast in a transmittable form of information that can be communicated or transmitted to other researchers or physicians or genetic counselors or patients. Such a form can vary and can be tangible or intangible. The result in the individual tested can be embodied in descriptive statements, diagrams, photographs, charts, images or any other visual forms. For example, images of gel electrophoresis of PCR products can be used in explaining the results. Diagrams showing where a variant occurs in an individual's allele are also useful in indicating the testing results. Statements regarding the presence of an AIR marker or polymorphism are also useful in indicating the testing results. These statements and visual forms can be recorded on a tangible media such as papers, computer readable media such as floppy disks, compact disks, etc., or on an intangible media, e.g., an electronic media in the form of email or website on internet or intranet. In addition, the result can also be recorded in a sound form and transmitted through any suitable media, e.g., analog or digital cable lines, fiber optic cables, etc., via telephone, facsimile, wireless mobile phone, internet phone and the like. All such forms (tangible and intangible) would constitute a "transmittable form of information". Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present disclosure also encompasses a method for producing a transmittable form of information containing the presence or absence of an AIR marker or polymorphism in an individual. This form of information is useful for predicting the responsiveness of a patient having asthma, and for selectively treating a patient based upon that information.

Methods of Treatment and Uses of IL-13 Antagonists

The disclosed methods allow clinicians to provide a personalized therapy for asthma patients, i.e., they allow determination of whether to selectively treat the patient with an IL-13 antagonist. In this way, a clinician can maximize the benefit and minimize the risk of IL-13 antagnoism in the entire population of patients afflicted with asthma. It will be understood that IL-13 antagonists are useful for the treatment, prevention, or amelioration of asthma, including moderate or severe asthma. The IL-13 antagonists, may be used in vitro, ex vivo, or incorporated into pharmaceutical compositions and administered to individuals (e.g., human patients) in vivo to treat, ameliorate, or prevent asthma, e.g., in patients who have an AIR marker. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

The IL-13 antagonists, may be used as a pharmaceutical composition when combined with a pharmaceutically acceptable carrier. Such a composition may contain, in addition to an IL-13 antagonist, carriers, various diluents, fillers, salts, buffers, stabilizers, solubilizers, and other materials well known in the art. The characteristics of the carrier will depend on the route of administration.

Antibodies, e.g., antibodies to IL-13, are typically formulated either in aqueous form ready for parenteral administration or as lyophilisates for reconstitution with a suitable diluent prior to administration. In some embodiments of the disclosed methods and uses, the IL-13 antagonist, e.g., IL-13 antibody, is formulated as a lyophilisate. Suitable lyophilisate formulations can be reconstituted in a small liquid volume (e.g., 2 ml or less) to allow subcutaneous administration and can provide solutions with low levels of antibody aggregation. The use of antibodies as the active ingredient of pharmaceuticals is now widespread, including the products HERCEPTIN® (trastuzumab), RITUXAN® (rituximab), SYNAGIS® (palivizumab), etc. Techniques for purification of antibodies to a pharmaceutical grade are well known in the art. When a therapeutically effective amount of an IL-13 antagonist is administered by intravenous, cutaneous or subcutaneous injection, the IL-13 antagonist will be in the form of a pyrogen-free, parenterally acceptable solution. A pharmaceutical composition for intravenous, cutaneous, or subcutaneous injection may contain, in addition to the IL-13 antagonist, an isotonic vehicle such as sodium chloride, Ringer's, dextrose, dextrose and sodium chloride, lactated Ringer's, or other vehicle as known in the art.

The appropriate dosage will, of course, vary depending upon, for example, the particular IL-13 antagonists to be employed, the host, the mode of administration and the nature and severity of the condition being treated, and on the nature of prior treatments that the patient has undergone. Ultimately, the attending health care provider will decide the amount of the IL-13 antagonist with which to treat each individual patient.

In practicing some of the methods of treatment or uses of the present disclosure, a therapeutically effective amount of an IL-13 antagonist is administered to a patient, e.g., a mammal (e.g., a human). While it is understood that the disclosed methods provide for selective treatment of patients depending on the presence of an AIR marker, this does not preclude that, if the patient is ultimately treated with an IL-13 antagonist, such IL-13 antagonist therapy is necessarily a monotherapy. Indeed, if a patient is selected for treatment with an IL-13 antagonist, then the IL-13 antagonist may be administered in accordance with the method of the disclosure either alone or in combination with other therapeutics for treating asthma. When coadministered with one or more additional therapeutics, an IL-13 antagonist may be administered either simultaneously with the other therapeutic, or sequentially. If administered sequentially, the attending physician will decide on the appropriate sequence of administering the IL-13 antagonist in combination with other therapeutics, as well as the appropriate dosages for co-delivery.

An IL-13 antagonist, is conveniently administered parenterally, intravenously, e.g., into the antecubital or other peripheral vein, intramuscularly, or subcutaneously. The duration of intravenous (i.v.) therapy using a pharmaceutical composition of the present disclosure will vary, depending on the severity of the disease being treated and the condition and personal response of each individual patient. Also contemplated is subcutaneous (s.c.) therapy using a pharmaceutical composition of the present disclosure. The health care provider will decide on the appropriate duration of i.v. or s.c. therapy and the timing of administration of the therapy, using the pharmaceutical composition of the present disclosure.

Doses may be delivered based on weight, e.g., 3 mg/kg, 10 mg/kg, 15 mg/kg, or as a fixed amount, e.g., 75 mg, 150 mg, 300 mg, 1000 mg depending on the severity of the disease.

Kits

The invention also encompasses kits for detecting an AIR marker or polymorphism, expression level, protein level or activity, in a biological sample (a test sample) from an asthma patient. Such kits can be used to predict if a patient having asthma is likely to respond (or have a higher response) to treatment with an IL-13 antagonist. For example, the kit can comprise a probe (e.g., an oligonucleotide, antibody, labeled compound or other agent) capable of detecting an AIR marker or polymorphism, products of those alleles and/or an equivalent genetic marker of those alleles in a biological sample. The kit may also comprise instructions for providing a prediction of the likelihood that the patient will respond to treatment with the IL-13 antagonist.

Probes may specifically hybridize to genomic sequences, nucleic acid products, or polypeptide products. Exemplary probes are oligonucleotides or conjugated oligonucleotides that specifically hybridizes to the responsive alleles of Table 1; an antibody that is capable of differentiating between polypeptide products encoded by the disclosed alleles; primer-extension oligonucleotides, allele-specific primers, a combination of allele-specific primers, allele-specific probes, and primer extension primers, etc. Optionally, the kit can contain a probe that targets an internal control allele, which can be any allele presented in the general population. Detection of an internal control allele is designed to assure the performance of the kit. The disclosed kits can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

Such kits may also comprise an IL-13 antagonist or a pharmaceutical composition comprising the IL-13 antagonist. Such kits are useful in the selective treatment of asthma patients using an IL-13 antagonist. Additionally, such kits may comprise means for administering the IL-13 antagonist (e.g., a syringe and vial, a prefilled syringe, a prefilled pen) and instructions for use. These kits may contain additional therapeutic agents for treating asthma, e.g., for delivery in combination with the enclosed IL-13 antagonist.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, etc. With such items, a patient may self-administer the drug (i.e., administer the drug on their own behalf) or a physician may administer the drug.

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All numerical ranges in this disclosure are inclusive of the endpoints and of all integers, decimals and fractions therebetween whether specifically stated or not. All patents and publications cited in this specification are incorporated by reference. The following Examples are presented in order to more fully illustrate the preferred embodiments of the disclosure. These examples should in no way be construed as limiting the scope of the disclosed patient matter, as defined by the appended claims.

EXAMPLES

List of Abbreviations

| Abbreviation | Explanation |
| --- | --- |
| ACQ | Asthma Control Questionnaire |
| DNA | Deoxyribonucleic Acid |
| FEV | Forced Expiratory Volume |
| IgE | Immunoglobulin E |
| IL-4 | Interleukin 4 |
| IL4-Rα | Interleukin 4 Receptor, Alpha |
| IL-13 | Interleukin 13 |
| LD | Linkage Disequilibrium |
| SNP | Single Nucleotide Polymorphism |
| UTR | Untranslated Region |

Example 1

Identification of IL-13 Antagonists

For the purposes of the invention, IL-13 antagonists that compete with a specified anti-IL-13 antibody set forth herein, including antibody 01951/G12 (SEQ ID NO:14 and 16) for binding to IL-13 can be identified by methods known in the art, and further as described in the following methodology.

All experiments are performed using a Biacore T200 instrument. Biacore T200 Control software and Biacore T200 Evaluation software are used for the control and analysis of experiments, respectively.

PART 1: The anti-human IL-13 antibody ANTIBODY 01951/G12 is immobilized to a CM5 sensorchip surface using the amine coupling method. Briefly, the surface of the measuring flow cell is activated with EDC/NHS, followed by a 700 second addition of 50 µg/mL ANTIBODY 01951/G12 in 10 mM sodium acetate pH 4.5. Based on previous experiments, these buffers and injection times are sufficient to allow saturation of the chip surface with ANTIBODY 01951/G12, though exposure time could be reduced if saturation was achieved prior to 700 seconds. Immobilization buffers that are potentially more suitable could be determined by buffer scouting. Any remaining active surface groups are subsequently blocked with ethanolamine. The surface of the reference flow cell is activated with EDC/NHS and subsequently blocked with ethanolamine without immobilization of protein (blank immobilization) or by the addition of an isotype control antibody. Based on previous studies using ANTIBODY 01951/G12 immobilization, an appropriate running buffer is HBS-EP+ containing 10 mM HEPES, 150 mM NaCl, 0.005% (w/v) polysorbate 20 and 3 mM EDTA at pH 7.4.

PART 2: A concentration-response curve for human IL-13 is performed to determine the appropriate concentration of IL-13 to use in the subsequent epitope competition studies. IL-13 is diluted in running buffer and, beginning at 25 nM, is flowed over the reference and measuring flow cell at a flow rate of 30 µL/min. The optimal rate can be adjusted experimentally. The association time is 120 seconds and dissociation time is 120 seconds, although dissociation time could be extended to 180 seconds, or 600 seconds or more if an affinity ($K_D$) measurement is required. Regeneration of the surface with a 30 second injection of 10 mM Glycine at pH 2.0, at a flow rate of 10 µL/min, is necessary to remove IL-13 from ANTIBODY 01951/G12 after the dissociation step. A second regeneration step immediately after the first is sometimes required. These steps are repeated over the following dilution series of IL-13: 25, 12.5, 6.25, 3.13, 1.56 and 0 nM. Based on previous studies, this dilution series would be suitable for preliminary experiments, but may need to be changed accordingly. The dilution series is run twice to provide n=2. Analysis temperature is 25° C. Running buffer is HBS-P+ containing 10 mM HEPES, 150 mM NaCl, 0.005% (w/v) and polysorbate 20 at pH 7.4. Data is evaluated using a 1:1 binding model with Biacore T200 Evaluation software.

PART 3: Epitope competition studies are done using a dual binding method. Based on the data from Part 2, a concentration of IL-13 that gives approximately 50 RU binding to ANTIBODY 01951/G12 is injected for 120 seconds at 30 µL/min. There is NO dissociation phase; instead a second injection of a competitor anti-IL-13 antibody immediately follows, at a 10-fold* greater concentration than IL-13. Previous studies with respect to IL-25 have used an association phase of 120 seconds, with a flow rate of 30 µL/min, mirroring the IL-13 addition. Any competitor that binds to IL-13 using a different epitope to that of ANTIBODY 01951/G12 will give a binding response. Those that bind to IL-13 using the same epitope as ANTIBODY 01951/G12 will give no binding response. A variable dissociation period can apply, followed by an acidic wash step to remove both the IL-13 and the competitor addition. This step can be reversed, with competitor antibody immobilized to the chip surface and ANTIBODY 01951/G12 as the second addition, to confirm results. Running buffer is HBS-P+ containing 10 mM HEPES, 150 mM NaCl, 0.005% (w/v) and polysorbate 20 at pH 7.4.

Example 2

Identification of the Antibody 01951/G12 Epitope Residues: Peptide Mapping:

The sequence of IL-13 was probed at the peptide level to identify the binding site with ANTIBODY 01951/G12. Thirty four 15-mer peptides were synthesized in order to scan the entire sequence with 12 residue overlap starting from the N-terminus. The synthesis of the peptides, preparation of the peptide-array slides, incubation with antibodies and data analysis where done as described by Maksimov et al. (PLoS ONE 7(3): e34212).

The results are shown in Table 4. The binding signal intensity (light unit) observed is reported for each peptide, in column 1 against a control unrelated human antibody and in column 2 against ANTIBODY 01951/G12. Signals above 10000 Light Units are considered as being significant. 2 overlapping peptides in the set of the 34 peptides produced a signal above that threshold, peptide 22 (TQRMLSGFCPHKVSA) (SEQ ID NO: 31) and peptide 23 (MLSGFCPHKVSAGQF) (SEQ ID NO: 32). The overlapping sequence between both peptides is MLSGFCPHKVSA (SEQ ID NO: 33).

In order to verify that this sequence is important for the binding of IL-13 to ANTIBODY 01951/G12 and eventually narrow it down further, a substitution analysis was performed. For this substitution analysis, a peptide array was created where each residue of the sequence MLSGFCPHKVSA was exchanged against every possible 20 standard amino acid, creating a set of 240 peptides in which 228 peptides differ from the original sequence by 1 amino acid at a time. The result of the binding study with ANTIBODY 01951/G12 is presented in FIG. 1. The boxed region indicates residues for which binding is strongly reduced or abolished when they are replaced by almost any amino acid. Therefore this sequence stretch, FCPHKV (SEQ ID NO: 67), represent the minimal binding region of IL-13 to ANTIBODY 01951/G12.

Sequence of IL-13 Used for Peptide Mapping:

```
                                          (SEQ ID NO: 34)
SPGPVPPSTALRELIEELVNITQNQKAPLCNGSMVWSINLTAGMYCAALE
SLINVSGCSAIEKTQRMLSGFCPEIKVSAGQFSSLHVRDTKIEVAQFVKD
LLLEILKKLFREGRFN.
```

TABLE 4

Signal intensities (Light Unit) of peptides of IL-13 of control antibody and target antibody (ANTIBODY 01951/G12) incubations.

| Index | peptide sequence | SEQ ID NO: | Corrected Mean control- antibody | Corrected Mean ANTIBODY 01951/G12 |
|---|---|---|---|---|
| 1 | SPGPVPPSTALRELI | 35 | 44.3 | -1072.3 |
| 2 | PVPPSTALRELIEEL | 36 | -9 | -1133.3 |
| 3 | PSTALRELIEELVNI | 37 | -7.3 | -210.5 |
| 4 | ALRELIEELVNITQN | 38 | -16.7 | -207 |
| 5 | ELIEELVNITQNQKA | 39 | -2.7 | -131 |
| 6 | EELVNITQNQKAPLC | 40 | 1.5 | 1 |
| 7 | VNITQNQKAPLCNGS | 41 | 28 | -405 |
| 8 | TQNQKAPLCNGSMVW | 42 | 41.7 | -350.5 |
| 9 | QKAPLCNGSMVWSIN | 43 | 27.7 | -518 |
| 10 | PLCNGSMVWSINLTA | 44 | -6.5 | -982 |
| 11 | NGSMVWSINLTAGMY | 45 | -5 | -131.5 |
| 12 | MVWSINLTAGMYCAA | 46 | 19 | 56.5 |
| 13 | SINLTAGMYCAALES | 47 | -1.5 | -757 |
| 14 | LTAGMYCAALESLIN | 48 | 1 | -99.7 |
| 15 | GMYCAALESLINVSG | 49 | 1 | -987 |
| 16 | CAALESLINVSGCSA | 50 | 1 | -586.7 |
| 17 | LESLINVSGCSAIEK | 51 | 18.7 | -340.3 |
| 18 | LINVSGCSAIEKTQR | 52 | 12.5 | -539.3 |
| 19 | VSGCSAIEKTQRMLS | 53 | 15 | -830.3 |
| 20 | CSAIEKTQRMLSGFC | 54 | 26 | -721.3 |
| 21 | IEKTQRMLSGFCPHK | 55 | 101 | 2207 |
| 22 | TQRMLSGFCPHKVSA | 31 | 123 | 38568 |
| 23 | MLSGFCPHKVSAGQF | 32 | 23 | 48125.7 |
| 24 | GFCPHKVSAGQFSSL | 56 | 3.3 | 492.7 |
| 25 | PHKVSAGQFSSLHVR | 57 | -24.7 | -386.5 |
| 26 | VSAGQFSSLHVRDTK | 58 | 3.7 | -778.5 |
| 27 | GQFSSLHVRDTKIEV | 59 | -10.5 | -291 |
| 28 | SSLHVRDTKIEVAQF | 60 | -6 | -170 |
| 29 | HVRDTKIEVAQFVKD | 61 | -17 | -734.3 |
| 30 | DTKIEVAQFVKDLLL | 62 | -13 | -438.5 |
| 31 | IEVAQFVKDLLLHLK | 63 | -11 | -810 |
| 32 | AQFVKDLLLHLKKLF | 64 | 25 | -746.5 |
| 33 | VKDLLLHLKKLFREG | 65 | 19 | -203 |
| 34 | LLLHLKKLFREGRFN | 66 | 322 | 7152.3 |

Example 3

Pharmacogenetic Analysis of IL4-Rα SNPs and Discovery of AIR Markers 1-9:

ANTIBODY 01951/G12 is a fully human IgG1/κ monoclonal antibody. CQAX576A2207 was a Phase II clinical study to evaluate the effectiveness and safety of ANTIBODY 01951/G12 in patients with moderate to severe persistent asthma following multiple doses, when added to existing asthma therapy.

To assess associations of several single nucleotide polymorphisms (SNPs) in the IL4-Rα gene and risk of asthma exacerbation in patients treated with ANTIBODY 01951/G12, DNA was collected from patients enrolled in the CQAX576A2207 trial and nine SNPs in the IL4-Rα gene were genotyped in these samples. Statistical tests of association were performed to assess the evidence for association of SNPs in the IL4-Rα gene with risk of asthma exacerbation, as well as with other asthma clinical endpoints, in patients treated with ANTIBODY 01951/G12.

In this manner, a pharmacogenetic analysis was undertaken, with the objective:

To evaluate whether certain SNPs in the IL4-Rα gene are associated with risk of asthma exacerbation in patients treated with ANTIBODY 01951/G12.

To evaluate whether certain SNPs are associated with change from baseline in ACQ7 score, FEV1, or IgE level in patients treated with ANTIBODY 01951/G12.

To evaluate whether the aforementioned SNPs are associated with risk of asthma exacerbation in patients treated with placebo.

Study Population

The study population included all patients who met the following criteria:
Were included in the final analysis population of the CQAX576A2207 clinical study, and
Did not have a discrepancy between gender as recorded in the clinical database vs. as determined genetically

Clinical Endpoints Evaluated

Statistical tests were performed to evaluate evidence for association between IL4-Rα SNPs and the following asthma clinical endpoints:
Risk of occurrence of at least one asthma exacerbation from baseline to Week 24
Mean absolute change from baseline to Week 24 in ACQ7 score
Mean percent change from baseline to Week 24 in FEV1 level
Mean percent change from baseline to Week 24 in IgE level

Genetic Markers Evaluated

The following strategies were employed to identify genetic variants associated with response to ANTIBODY 01951/G12.
Candidate SNPs
The 9 SNPs utilized in this pharmacogenetic analysis are listed in Table 5 together with their location relative to the gene structure and, where applicable, their effect on the gene product. They are listed in their physical order along the gene. The SNPs were genotyped using the Taqman platform.

TABLE 5

| SNP | Reported association with pitrakinra exacerbation risk | Location | Effect |
|---|---|---|---|
| rs1110470 | yes | intron | unknown |
| rs3024530 | yes | intron | unknown |
| rs1805010 | yes | exon | amino acid change (I→V) |
| rs2239347 | yes | intron | unknown |
| rs1805011 | no | exon | amino acid change (E→A) |
| rs1801275 | no | exon | amino acid change (Q→R) |
| rs8832 | yes | 3' UTR | some UTR variants affect gene transcription level |
| rs1029849 | yes | 3' proximal | unknown |
| rs4787956 | yes | 3' proximal | unknown |

UTR, untranslated region

Genome-wide Association Study (GWAS)

A genome-wide association study (GWAS) was performed using the Illumina Omni5Exome chip. All SNPs that map to the IL4-Rα gene were evaluated.

Resequencing of the IL4-Rα Gene

Sanger sequencing was performed on most exons in the IL4-Rα gene, as well as the 3' untranslated region (UTR), to determine whether any additional variants could be identified that were not included on the Omni5Exome chip.

Genotyping Methods

Candidate SNPs

Sample Reactions were prepared following the Protocol recommended by the vendor, TaqMan SNP Genotyping Assays Protocol (PN 4332856D), and using Taqman Universal Master mix (PN 4326614), with the following exceptions:
2.00 uL of DNA sample per reaction
0.25 ul of Water was added per reaction
PCR reactions were conducted on the GeneAmp 9700 (Applied Biosystems) using the program specified in the vendor protocol with the following exception:
Standard thermal profile is used with 50 cycles, rather than 40
Endpoint reads were conducted on the ABI PRISM 7900HT Sequence Detection System, with data analysis by SNP Manager and SDS 2.2.2 (Applied Biosystems).

GWAS

Genotype data for the GWAS were generated using the Illumina HumanOMNI5Exome microarray platform.

Resequencing of the IL4-Rα Gene

SNPs were identified by Sanger sequencing in IL4Rα (NT_010393.15). PCR was performed using unique primers carrying M13 universal sequence tags. Amplicons for each coding region were bi-directionally sequenced with unique or universal primers and BigDye Terminator v3.1 (Applied Biosystems, 4337456). Sequencing products were cleaned up with CleanSEQ (Beckman, A29154) and run on a 3730xl Genetic Analyzer (Applied Biosystems) with POP-7 for sequence detection. Traces were aligned to reference sequences for each amplicon from NCBI using PhredPhrap (University of Washington) and were then visually inspected for discrepancies from canonical sequence using Consed (University of Washington, version 19.0). Sequence variations were noted and any corresponding coding changes characterized where possible.

Statistical Methods

Analysis of Asthma Exacerbation Risk

All tests of association between SNPs and risk of asthma exacerbations were conducted by way of a conditional logistic regression model using PROC LOGISTIC in SAS version 9.3, with country as the conditioning factor. All tests were designed to evaluate the hypothesis of an additive relationship between genotype and exacerbation risk (on the logit scale), meaning that the risk among heterozygotes is intermediate to that within the two homozygous classes. The additive hypothesis was tested by specifying genotype as a continuous variable equal to the number of copies of the minor (i.e., less common in the CQAX576A2207 sample) allele carried by the patient.

Race and ethnicity are known to be common confounding factors in genetic association studies; as such, it is advisable to adjust for race and ethnicity in association tests where possible. In the CQAX576A2207 study the distributions of race and ethnicity were too imbalanced to enable adjustment for these factors, so the logistic regression was instead conditioned on country as a proxy for those factors.

The score statistic was used to assess statistical significance. No adjustment was made for multiple testing.

Analysis of Change from Baseline in ACQ7, FEV1, and IgE

All tests for association between SNPs and absolute change from baseline in ACQ7, percent change from baseline in FEV1, and percent change from baseline in IgE were conducted by way of a linear model using PROC GENMOD in SAS version 9.3. All tests evaluated the hypothesis of an additive relationship between genotype and the endpoint, as described in Section 3.4.1. Country, history of atopy, maintenance oral corticosteroid use, and baseline level of the corresponding endpoint were included in the model as covariates. A Wald chi-square test was used to assess statistical significance. No adjustment was made for multiple testing.

Permutation Test to Assess Overall Significance

A permutation test was performed to assess the likelihood of finding that each of the top 7 SNPs in Table 5 (i.e. excluding the bottom 2 SNP's: rs1029849, and rs4787956) would be found to have a homozygous genotype class in which there were no exacerbations among ANTIBODY 01951/G12-treated patients, if in reality there were no association between any of the SNPs and ANTIBODY 01951/G12 exacerbation risk.

The permutation test proceeded according to the following steps:

For the first permutation, exacerbation status (yes/no) was randomly permuted for the 94 ANTIBODY 01951/G12-treated patients, such that it remained the case that only 12 of the 94 patients experience an exacerbation but these 12 patients were selected at random. All genotype data remained unchanged.

Using this permuted dataset, each SNP was evaluated to determine whether it had a homozygous genotype class in which there were no exacerbations. If all 7 SNPs were found to have such a genotype class, the permuted dataset was flagged to record that finding.

The first 2 steps were iterated 1000 times. The percentage of permuted datasets that were flagged to indicate that each of the 7 SNPs had a homozygous genotype class with no exacerbations represented the empirical significance level of this finding. Thus, a small percentage of flagged datasets would indicate a low likelihood of observing such a result by random chance, and would be taken as evidence that risk of asthma exacerbation among ANTIBODY 01951/G12-treated patients is influenced by SNPs in the IL4-Rα gene.

Calculation of r-squared Values in the Linkage Disequilibrium Graph

The $r^2$ values in the LD graph were computed using Haploview software (Barrett et al, 2004).

Cross-validation Analysis to Assess Optimal Number of SNPs for Prediction

Cross-validation is a statistical method that can be used to compare alternative approaches to building predictive models to assess which approach is most likely to yield the model with highest predictive accuracy. The method entails dividing the available set of patients into a training set and a test set, applying alternative model-building approaches to the training set only, using the resulting models to predict the outcome of the patients in the test set, and determining which model predicted most accurately. This procedure is repeated many times, the predictions are averaged across the test sets. If a particular approach tends to result in more accurate predictions than the other approaches, it suggests that this approach may also result in a model with the highest predictive accuracy when applied to future studies.

In this application of cross-validation, once the selected SNPs were determined for each of the model-building approaches listed below, linear discriminant analysis (LDA) was applied to build the predictive model. The set of markers available for selection consisted of 6 of the top 7 IL4-Rα SNPs listed in Table 5. rs3024530 was removed because it was almost perfectly correlated with rs1805010. The procedure was then applied to patients treated with ANTIBODY 01951/G12 to compare the following model-building approaches:

Include the most significant SNP from each of the 2 linkage disequilibrium (LD) blocks Include the 2 SNPs selected above, as well as the next most significant SNP Include the 2 most significant SNPs from each of the 2 LD blocks Include the 4 SNPs selected above, as well as the next most significant SNP Include all 6 SNPs.

The results were compared to evaluate whether a predictive model that includes additional SNPs would be likely to have substantially higher predictive accuracy than one which contains only the single most significant SNP from each of the 2 LD blocks.

Results:

Genotype Frequencies of IL4-Rα SNPs

A total of 94 ANTIBODY 01951/G12-treated patients and 102 placebo-treated patients were genotyped for the 9 SNPs in the IL4-Rα gene listed in Table 5. Two patients, both placebo-treated, had a discrepancy between gender as recorded in the clinical database vs. as determined genetically, and were removed from the analysis. Both were from the same country, suggesting a possible sample switch.

Twelve of the 94 ANTIBODY 01951/G12-treated patients (12.8%) experienced at least one asthma exacerbation during the study, compared to 23 of 100 placebo-treated patients (23.0%). The distribution was consistent with Hardy-Weinberg equilibrium for each SNP.

TABLE 0-1

Genotype frequency distributions in ANTIBODY 01951/G12 and pitrakinra studies

| SNP | Genotype frequency distribution | ANTIBODY 01951/G12 study n (%) |
|---|---|---|
| rs1110470 | GG | 61 (31.4%) |
|  | AG | 97 (50.0%) |
|  | AA | 36 (18.6%) |
| rs3024530 | AA | 48 (24.7%) |
|  | AG | 106 (54.6%) |
|  | GG | 40 (20.6%) |
| rs1805010 | AA | 47 (24.5%) |
|  | AG | 105 (54.7%) |
|  | GG | 40 (20.8%) |
| rs2239347 | AA | 48 (24.7%) |
|  | AC | 98 (50.5%) |
|  | CC | 48 (24.7%) |
| rs1805011 | AA | 159 (82.4%) |
|  | AC | 31 (16.1%) |
|  | CC | 3 (1.6%) |
| rs1801275 | AA | 127 (65.5%) |
|  | AG | 56 (28.9%) |
|  | GG | 11 (5.7%) |
| rs8832 | GG | 58 (29.9%) |
|  | AG | 93 (47.9%) |
|  | AA | 43 (22.2%) |
| rs1029849 | GG | 68 (35.2%) |
|  | AG | 86 (44.6%) |
|  | AA | 39 (20.2%) |
| rs4787956 | AA | 71 (36.6%) |
|  | AG | 99 (51.0%) |
|  | GG | 24 (12.4%) |

Genotype frequencies were calculated by combining the ANTIBODY 01951/G12 and placebo arms.

Association Between IL4-Rα SNPs and Risk of Exacerbation

The proportion of ANTIBODY 01951/G12-treated patients who experienced at least one asthma exacerbation during the study is shown in FIG. 2 by genotype class for each of the 9 genotyped SNPs, along with significance levels for the corresponding tests of association between SNP and exacerbation risk. Six of these 7 SNPs were also significantly associated with response to ANTIBODY 01951/G12, with p-values ranging from 0.005 to 0.015, while the remaining SNP approached significance with a p-value of 0.066. Moreover, the SNPs generally showed an additive effect on exacerbation risk in both studies, meaning that the risk for heterozygotes was generally intermediate to that for the two homozygous classes, suggesting that exacerbation risk for both therapies increases with the number of risk alleles carried by an individual at an associated SNP.

Since race is well known to be a common confounding factor in genetic association studies, the association tests for ANTIBODY 01951/G12-treated patients were repeated using only self-reported Caucasian patients, but the p-values were unchanged. This is likely because 89 of the 94 patients (94.7%) were Caucasian, and the 5 non-Caucasians were all from countries in which there were no exacerbations.

Of particular note in the ANTIBODY 01951/G12 study, for each of the 7 SNPs there was one homozygous class for which no exacerbations were observed among ANTIBODY 01951/G12-treated patients, a result that would be unlikely to occur by random chance.

The results for the two bottom SNPs listed in Table 5, which code for amino acid changes in the IL-4RA receptor, showed weaker evidence for association with p-values 0.091 and 0.10.

Figure 3:
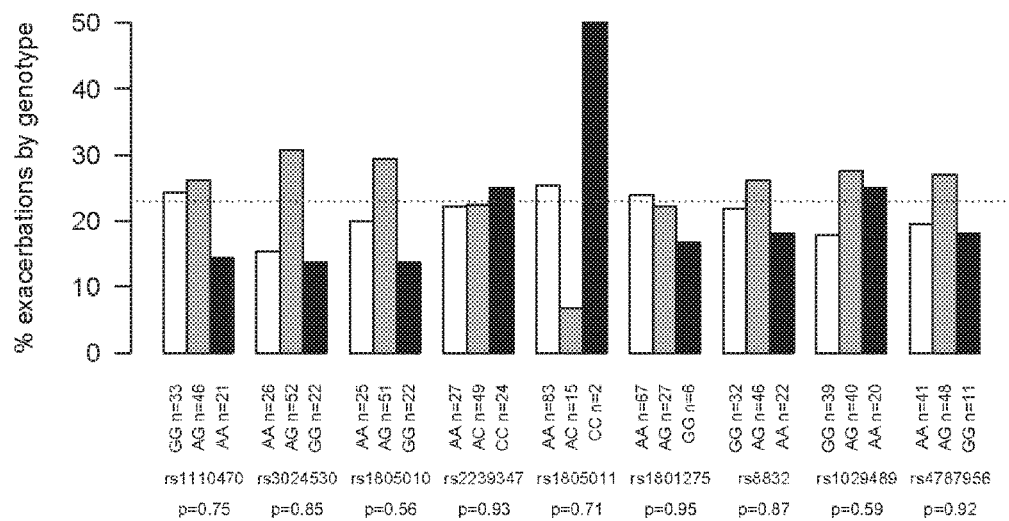
FIG. 3 depicts exacerbation risk by genotype class for placebo-treated patients in the ANTIBODY 01951/G12 study.

The proportion of placebo-treated patients in the ANTIBODY 01951/G12 study who experienced at least one asthma exacerbation is shown in FIG. 3 by genotype class for the 9 genotyped SNPs. Unlike the results for the ANTIBODY 01951/G12 arm, placebo-treated patients show no evidence of association between genotype and exacerbation risk for any of the SNPs.

The SNPs shown in all tables and figures for this pharmacogenetic analysis are ordered according to their physical location within the gene.

Association Between IL4-Rα SNPs and Other Asthma Endpoints

The 9 genotyped SNPs were also evaluated in ANTIBODY 01951/G12-treated patients for evidence of association with 3 other asthma endpoints: change from baseline in ACQ7 score, percent change from baseline in FEV1, and percent change from baseline in IgE. All endpoints were evaluated at Week 24. Since all association tests evaluated the hypothesis of an additive allelic effect (i.e., that the mean response among heterozygotes is intermediate to those of the two homozygous classes), FIG. 5 shows the effect of one additional copy of the minor allele (i.e., less common allele in this sample) on each of these 3 endpoints. For example, under the additive model, carrying one additional copy of the minor allele at rs8832—whether carrying 1 copy instead of 0, of 2 copies instead of 1—is associated with a mean increase from baseline in FEV1 of 7.6%. Thus, carrying 2 copies instead of 0 is associated with a mean increase of 15.2%.

The corresponding results for the asthma exacerbation endpoint are also provided for comparison. In this case the effect size represents the odds ratio associated with one additional copy of the minor allele. Hence, carrying one additional copy of the minor allele at rs8832 is associated with 3.8-fold increase in the odds of experiencing an exacerbation. Since odds ratios are multiplicative, carrying 2 copies instead of 0 is associated with a $3.8^2$, or 14.6-fold increase in odds of experiencing an exacerbation.

No SNPs attained or approached statistical significance for the ACQ7 or IgE endpoints, even without any adjustment for multiple testing. For the FEV1 endpoint, 4 SNPs attained significance, including a cluster of 3 SNPs with p<0.002 (rs8832, rs1029489, and rs4787956). However, the effect of these 3 SNPs on response to ANTIBODY 01951/G12 was in the opposite direction of that observed for asthma exacerbations: specifically, for each of the 3 SNPs the minor (less common in the sample) allele was associated with higher risk of exacerbation but also with a mean increase from baseline in FEV1. Another SNP, rs1110470, also attained borderline significance, but also in the opposite direction of that observed for exacerbations, and no other SNPs in its neighborhood attained or approached significance.

Permutation test to evaluate overall significance of exacerbation associations A permutation test was performed to evaluate how likely it would be to obtain association results similar to the ANTIBODY 01951/G12 exacerbation results if there were actually no association between the SNPs and exacerbation risk—i.e., as an artifact of random chance. Of particular interest was the finding that for each of the top 7 SNPs listed in Table 5, the ANTIBODY 01951/G12 analysis yielded one homozygous class in which there were no exacerbations; therefore, the permutation test was focused on how often this would be expected to occur by random chance. Among 1000 permuted datasets generated, only 2 yielded a result in which each of the 7 SNPs had one homozygous class with no exacerbations. Hence the probability of observing this result if there were no true associations was estimated to be 0.002.

Linkage Disequilibrium Analysis of the SNPs

Alleles that are located near each other on a chromosome tend to be inherited together. When these alleles also have similar population frequencies, they are likely to be correlated with each other, such that knowing a subject's genotype at a given SNP can enable one to predict the same subject's genotype at a nearby SNP with relatively high accuracy. This concept is referred to as "linkage disequilibrium" (LD). The relevance to genetic association studies is that multiple SNPs in a small region may show evidence of association with a phenotype; however, because these SNPs may be in LD with each other, any given SNP may not provide a substantial amount of independent evidence of association with the phenotype beyond that already obtained from other nearby SNPs.

Figure 4:
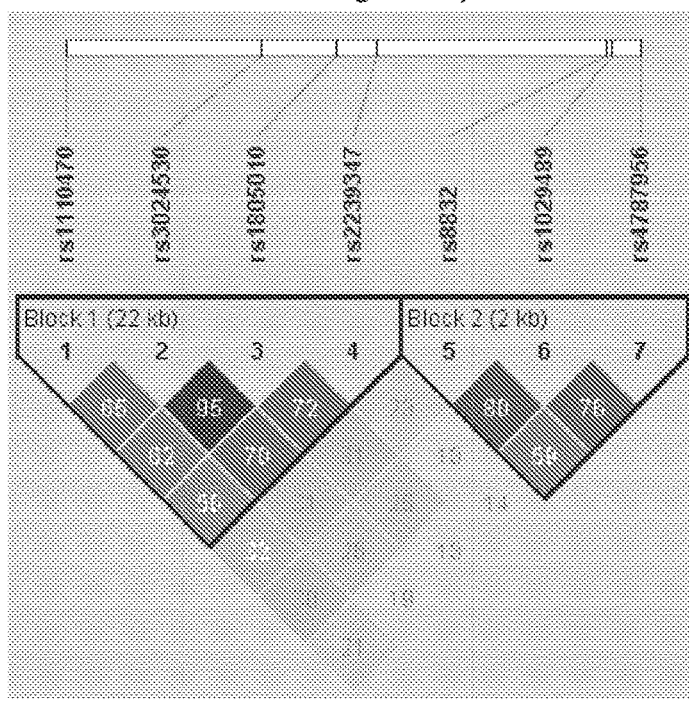
FIG. 4 depicts identification of two linkage disequilibrium blocks among IL4-Rα SNPs.

LD is known to occur in a "block" structure throughout the genome. Each block, or "cluster", contains a group of SNPs such that the correlations between pairs of SNPs within the same block are relatively high whereas the correlations between pairs of SNPs in different blocks are relatively low. An analysis of LD between the top 7 SNPs listed in Table 5 and ANTIBODY 01951/G12 exacerbation risk revealed the presence of 2 LD blocks, as illustrated in FIG. 4. The numerical values in the cell represent the $r^2$ value (multiplied by 100), a standard measure of correlation—or strength of LD—between the corresponding pair of SNPs. An $r^2$ value of 100 indicates that 2 SNPs are perfectly correlated, while 0 indicates complete independence.

As can be seen from the figure, the first 4 SNPs form one block, within which correlations between pairs of SNPs range from 56 to 95. SNPs rs3024530 and rs1805010 are almost perfectly correlated. The last 3 SNPs form the second block, with pairwise correlations ranging from 59 to 80. In contrast, no SNP from the first block shows high correlation with any SNP from the second block, the highest pairwise correlation being 32.

Cross-validation Analysis to Assess Optimal Number of SNPs for Prediction

A cross-validation analysis was conducted to compare strategies for utilizing the 6 of the top 7 IL4-Rα SNPs listed in Table 5 (rs3024530 was excluded because it was nearly perfectly correlated with rs1805010) to predict a patient's risk of asthma exacerbation after treatment with ANTIBODY 01951/G12. Because the LD analysis identified 2 largely independent blocks of SNPs that each show evidence of association with exacerbation risk, it is reasonable to expect that a predictive model with representation from both blocks would likely have greater ability to identify patients at low risk of exacerbation than one with representation from only one block. However, this raised the question of whether it would be sufficient to select only one SNP from each block or whether it would be beneficial to include additional SNPs. The cross-validation analysis showed that the expected ability of a predictive model to identify patients at low risk of asthma exacerbation would not improve substantially if additional SNPs were included beyond one from each block.

Additional Information

Genotype frequency distributions for the 7 SNPs are listed by country and ethnic population in FIGS. 6 and 7.

The 7 top SNPs listed in Table 5 were found in this study to associate with exacerbation risk among patients treated with ANTIBODY 01951/G12. Six of the 7 SNPs yielded significant p-values ranging from 0.005 to 0.015, while the remaining SNP approached significance. The same p-values were obtained when the analysis was restricted to Caucasian patients to mitigate the risk of confounding. Moreover, the particular pattern of association with response to ANTIBODY 01951/G12 with most SNPs exhibited an additive relationship with exacerbation risk; i.e., the risk within heterozygotes was observed to be intermediate to that within the 2 homozygous classes. Finally, it was observed that among ANTIBODY 01951/G12-treated patients each of the 7 SNPs had a particular homozygous class in which there were no exacerbations. A permutation test showed that the probability of observing this result in the absence of any true associations is 0.002. Taken together, along with the importance of the IL4-Rα gene to the mechanism of ANTIBODY 01951/G12, these results suggest a strong likelihood that the risk of asthma exacerbations in patients treated with ANTIBODY 01951/G12 is influenced by SNPs in the IL4-Rα gene.

In addition, the two other SNPs in the IL4-Rα gene (listed as bottom two SNPs in Table 5) were evaluated for possible association with exacerbation risk in ANTIBODY 01951/G12-treated patients because of their reported association with asthma disease phenotypes and because they code for amino acid changes. Although, both were less significant than the other 7 SNPs (p=0.091 and 0.10).

No evidence was found for association between SNPs in the IL4-Rα gene and exacerbation risk among patients treated with placebo in the ANTIBODY 01951/G12 study. Taken together with knowledge of the ANTIBODY 01951/G12 mechanism, this suggests that the influence of these SNPs on exacerbation risk is specific to the drug mechanism and is not reflective of a more general disease severity association. Moreover, no evidence was found for association between these SNPs and change from baseline in ACQ7 score or IgE level, and only a few SNPs were significantly associated with change in FEV1, with these associations pointing in the opposite direction of that seen for exacerbation risk. This suggests that the genetic mechanism influencing patient's susceptibility to exacerbations is different from that for other asthma endpoints.

The strong evidence for this pharmacogenetic association among ANTIBODY 01951/G12-treated patients suggests the use of particular genotypes or combination of genotypes at these SNPs to predict a patient's risk of asthma exacerbation after treatment with ANTIBODY 01951/G12.

As shown in Table 5, rs1805010 causes an amino acid substitution, while rs8832 is in the 3' untranslated region (UTR), a region known to influence gene transcription levels. Since rs1805010 lies in the first LD block while rs8832 lies in the second, these 2 SNPs are useful in developing a predictive model for exacerbation risk. The cross-tabulated genotype frequencies for these 2 SNPs in the CQAX576A2207 study are shown in Table 9.

TABLE 9

Cross-tabulated genotype frequencies for rs1805010 and rs8832 in the rs8832

| | | GG (lower exacerbation risk) | AG | AA (higher exacerbation risk) |
|---|---|---|---|---|
| rs1805010 | AA (lower exacerbation risk) | 33 (17.2%) | 9 (4.7%) | 5 (2.6%) |
| | AG | 20 (10.4%) | 71 (37.0%) | 14 (7.3%) |
| | GG (higher exacerbation risk) | 5 (2.6%) | 11 (5.7%) | 24 (12.5%) |

Genotype frequencies were calculated by combining the ANTIBODY 01951/G12 and placebo arms.

Example 4

Figure 8:
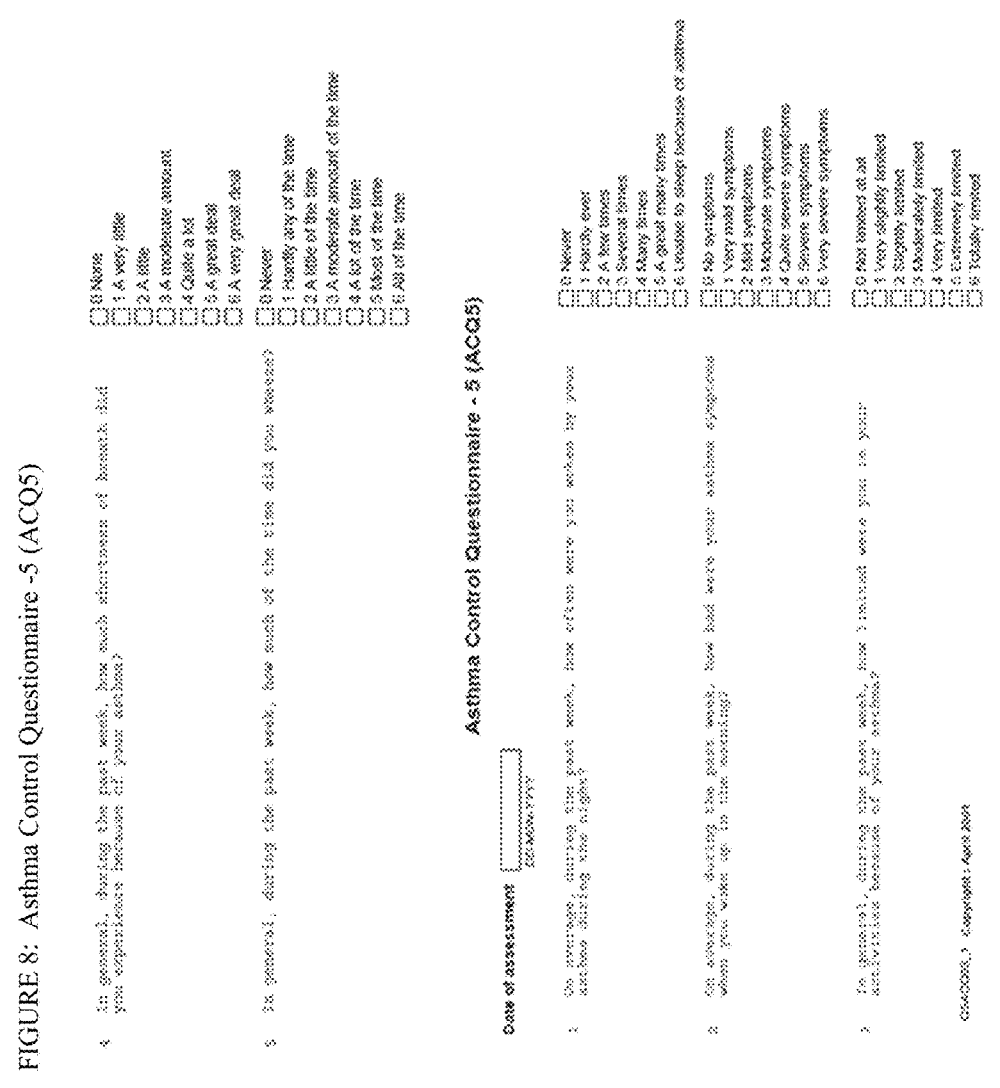
Figure 9:
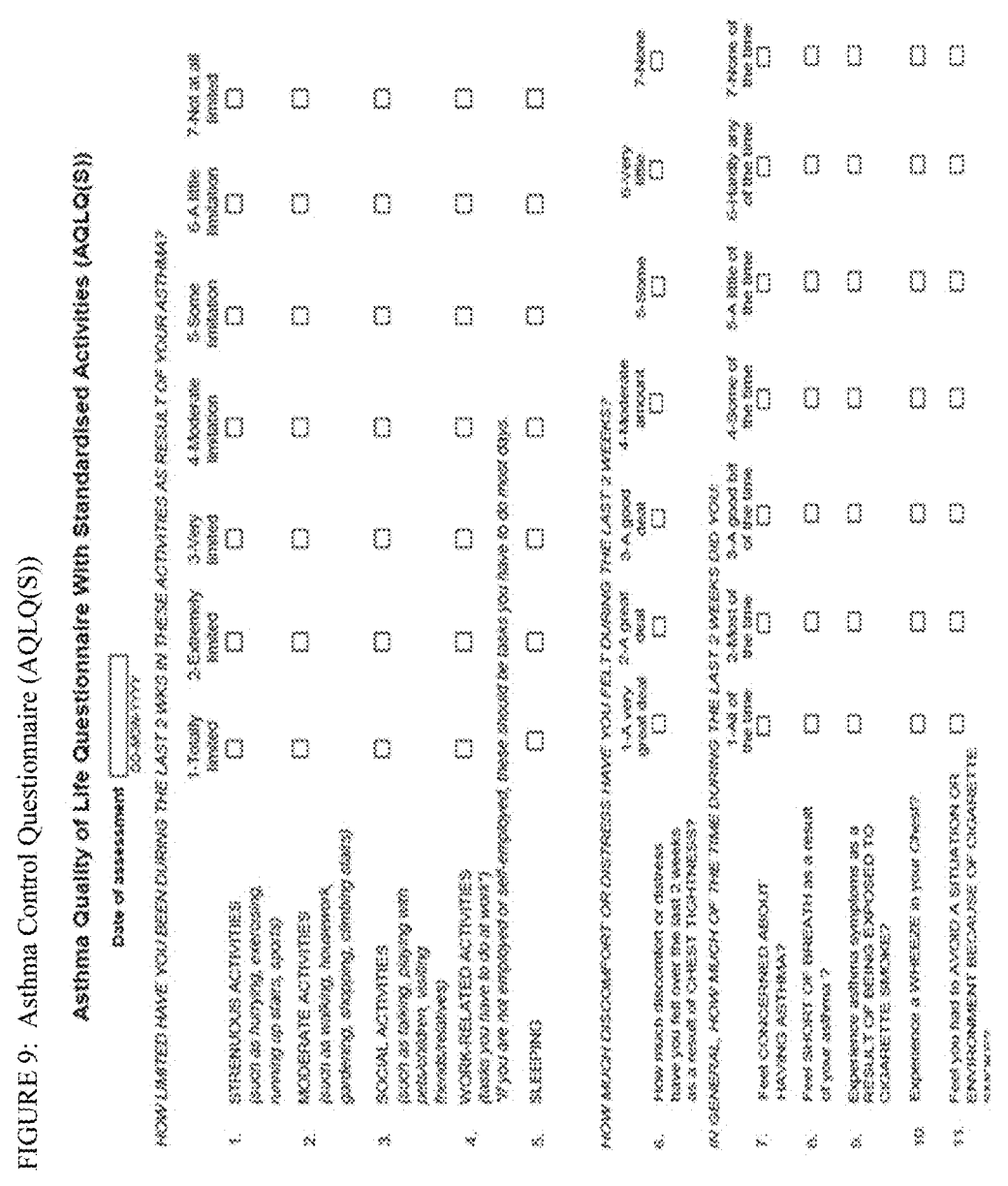

Methods to evaluate reduction in asthma exacerbations will be known to the skilled practitioner and include use of ACQ-5 and/or AQLQ-S as detailed in FIGS. 8 and 9.

---

What is claimed is:

1. A method of selectively treating a patient having asthma, comprising
   i) measuring one or more Anti-IL-13 Response ("AIR") markers selected from the group consisting of AIR marker 1, 2, 3, 4, 5, 6, 7, 8, and 9,
   ii) diagnosing whether the patient has asthma when one or more markers is present; and
   iii) thereafter administering a therapeutically effective amount of an IL-13 antagonist to the patient;
      wherein said IL-13 antagonist is an antibody comprising a heavy chain as set forth in SEQ ID NO: 20 and a light chain as recited in SEQ ID NO: 18.

2. The method according to claim 1, wherein
said measuring step comprises assaying a biological sample from the patient for the presence of at least one AIR marker selected from said group.

3. The method of claim 1 further comprising determining whether said AIR marker is present in homozygous or heterozygous form; wherein the step of diagnosing whether the patient has asthma is determined by the presence of the at least one AIR marker in homozygous form.

4. The method of claim 1, wherein said AIR marker is selected from the group consisting of AIR marker 3 and AIR marker 7.

5. The method according to claim 2, wherein the step of assaying comprises assaying the biological sample for a nucleic acid product of the at least one AIR marker, or a polypeptide product of the at least one AIR marker.

6. The method according to claim 2, wherein the step of assaying comprises assaying the biological sample for a genomic sequence of the at least one AIR marker.

7. The method according to claim 2, wherein the biological sample is selected from the group consisting of blood, serum, feces, plasma, urine, tear, saliva, and a tissue sample.

8. The method according claim 2, wherein the step of assaying comprises a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, high-density oligonucleotide SNP arrays, restriction fragment length polymorphism (RFLP) assays, primer extension assays, oligonucleotide ligase assays, analysis of single strand conformation polymorphism, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

9. The method according to claim 1, wherein said IL-13 antagonist is an antibody administered at a dose of about 50-1000 mg i.v. administered every 4 weeks.

10. The method according to claim 1, wherein the IL-13 antagonist has a $K_D$ of about 100-200 pM.

11. The method according to claim 1, wherein the IL-13 antagonist has an in vivo half-life of about 21 days.

* * * * *

```
                       SEQUENCE LISTING

<160> NUMBER OF SEQ ID NOS: 67

<210> SEQ ID NO 1
<211> LENGTH: 146
<212> TYPE: PRT
<213> ORGANISM: Homo sapiens

<400> SEQUENCE: 1

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Arg
    130                 135                 140

Phe Asn
145

<210> SEQ ID NO 2
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Phe Thr Phe Ser Ser Tyr Gly
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Ile Trp Tyr Asp Gly Ser Asn
1               5

<210> SEQ ID NO 4
```

<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 4

Ala Arg Leu Trp Phe Gly Asp Leu Asp
1               5

<210> SEQ ID NO 5
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 5

Ser Tyr Gly Met His
1               5

<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 6

Ile Ile Trp Tyr Asp Gly Ser Asn Lys Tyr Tyr Ala Asp Ser Val Lys
1               5                   10                  15

Gly

<210> SEQ ID NO 7
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 7

Leu Trp Phe Gly Asp Leu Asp Ala Phe Asp Ile
1               5                   10

<210> SEQ ID NO 8
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Gln Ser Val Ser Ser Tyr
1               5

<210> SEQ ID NO 9
<211> LENGTH: 2
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Asp Ala
1

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gln Gln Arg Ser Ser Trp Pro Pro Val
1               5

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ala Gly Gln Ser Val Ser Ser Tyr Leu Val
1               5                   10

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ala Ser Asn Arg Ala Thr
1               5

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln Gln Arg Ser Ser Trp Pro Pro Val Tyr Thr
1               5                   10

<210> SEQ ID NO 14
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 14

| Glu | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Ser | Ser | Tyr |
|---|---|---|---|---|---|---|---|---|---|---|---|---|---|---|---|
| | | | 20 | | | | | 25 | | | | | 30 | | |

| Gly | Met | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Ile | Ile | Trp | Tyr | Asp | Gly | Ser | Asn | Lys | Tyr | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Leu | Trp | Phe | Gly | Asp | Leu | Asp | Ala | Phe | Asp | Ile | Trp | Gly | Gln |
|---|---|---|---|---|---|---|---|---|---|---|---|---|---|---|---|
| | | | 100 | | | | | 105 | | | | | 110 | | |

| Gly | Thr | Met | Val | Thr |
|---|---|---|---|---|
| | | 115 | | |

<210> SEQ ID NO 15
<211> LENGTH: 351
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(351)

<400> SEQUENCE: 15

```
gaa gtg cag ctg gtg gag tct ggg gga ggc gtg gtc cag cct ggg agg     48
Glu Val Gln Leu Val Glu Ser Gly Gly Gly Val Val Gln Pro Gly Arg
1               5                   10                  15 tcc ctg aga ctc tcc tgt gca gcg tct gga ttc acc ttc agt agc tat     96
Ser Leu Arg Leu Ser Cys Ala Ala Ser Gly Phe Thr Phe Ser Ser Tyr
            20                  25                  30 ggc atg cac tgg gtc cgc cag gct cca ggc aag ggg ctg gag tgg gtg    144
Gly Met His Trp Val Arg Gln Ala Pro Gly Lys Gly Leu Glu Trp Val
        35                  40                  45 gca att ata tgg tat gat gga agt aat aaa tac tat gcg gac tcc gtg    192
Ala Ile Ile Trp Tyr Asp Gly Ser Asn Lys Tyr Tyr Ala Asp Ser Val
 50                  55                  60 aag ggc cga ttc acc atc tcc aga gac aat tcc aag aac acg ctg tat    240
Lys Gly Arg Phe Thr Ile Ser Arg Asp Asn Ser Lys Asn Thr Leu Tyr
65                  70                  75                  80 ctg caa atg aac agc ctg aga gcc gag gac acg gct gtg tat tac tgt    288
Leu Gln Met Asn Ser Leu Arg Ala Glu Asp Thr Ala Val Tyr Tyr Cys
            85                  90                  95 gcg agg cta tgg ttc ggg gac tta gat gct ttt gat atc tgg ggc caa    336
Ala Arg Leu Trp Phe Gly Asp Leu Asp Ala Phe Asp Ile Trp Gly Gln
        100                 105                 110 ggg aca atg gtc acc                                                351
Gly Thr Met Val Thr
            115
```

<210> SEQ ID NO 16
<211> LENGTH: 104
<212> TYPE: PRT

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Glu Ile Val Leu Thr Gln Ser Pro Ala Thr Leu Ser Leu Ser Pro Gly
1               5                   10                  15

Glu Arg Ala Ile Leu Ser Cys Arg Ala Gly Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Pro
                85                  90                  95

Val Tyr Thr Phe Gly Gln Gly Thr
            100
```

<210> SEQ ID NO 17
<211> LENGTH: 312
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(312)

<400> SEQUENCE: 17

```
gaa att gtg ttg acg cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc atc ctc tcc tgc agg gcc ggt cag agt gtt agc agt tac      96
Glu Arg Ala Ile Leu Ser Cys Arg Ala Gly Gln Ser Val Ser Ser Tyr
            20                  25                  30 tta gtc tgg tac caa cag aaa cct ggc cag gct ccc agg ctc ctc atc     144
Leu Val Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgc agc agc tgg cct ccg     288
Glu Asp Phe Ala Val Tyr Tyr Cys Gln Gln Arg Ser Ser Trp Pro Pro
                85                  90                  95 gtg tac act ttt ggc cag ggg acc                                     312
Val Tyr Thr Phe Gly Gln Gly Thr
            100
```

<210> SEQ ID NO 18
<211> LENGTH: 236
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Ser Val Leu Thr Gln Val Leu Ala Leu Leu Leu Trp Leu Thr
1               5                   10                  15

Gly Thr Arg Cys Glu Ile Val Leu Thr Gln Ser Pro Ala Thr Leu Ser
                20                  25                  30

Leu Ser Pro Gly Glu Arg Ala Ile Leu Ser Cys Arg Ala Gly Gln Ser
            35                  40                  45

Val Ser Ser Tyr Leu Val Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Ser Trp Pro Pro Val Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 19
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: CDS
<222> LOCATION: (1)..(711)

<400> SEQUENCE: 19 atg agt gtg ctc act cag gtc ctg gcg ttg ctg ctg ctg tgg ctt aca      48
Met Ser Val Leu Thr Gln Val Leu Ala Leu Leu Leu Leu Trp Leu Thr
1               5                   10                  15 ggt acg cgt tgt gaa att gtg ttg acg cag tct cca gcc acc ctg tct      96
Gly Thr Arg Cys Glu Ile Val Leu Thr Gln Ser Pro Ala Thr Leu Ser
            20                  25                  30 ttg tct cca ggg gaa aga gcc atc ctc tcc tgc agg gcc ggt cag agt     144
Leu Ser Pro Gly Glu Arg Ala Ile Leu Ser Cys Arg Ala Gly Gln Ser
        35                  40                  45 gtt agc agt tac tta gtc tgg tac caa cag aaa cct ggc cag gct ccc     192
Val Ser Ser Tyr Leu Val Trp Tyr Gln Gln Lys Pro Gly Gln Ala Pro

|  |  |  |  |  |  |  |  |  |  |  |  |  |  |  |  |
|---|---|---|---|---|---|---|---|---|---|---|---|---|---|---|---|

```
                    50                  55                  60
agg ctc ctc atc tat gat gca tcc aac agg gcc act ggc atc cca gcc      240
Arg Leu Leu Ile Tyr Asp Ala Ser Asn Arg Ala Thr Gly Ile Pro Ala
 65                  70                  75                  80 agg ttc agt ggc agt ggg tct ggg aca gac ttc act ctc acc atc agc      288
Arg Phe Ser Gly Ser Gly Ser Gly Thr Asp Phe Thr Leu Thr Ile Ser
                 85                  90                  95 agc cta gag cct gaa gat ttt gca gtt tat tac tgt cag cag cgt agc      336
Ser Leu Glu Pro Glu Asp Phe Ala Val Tyr Tyr Cys Gln Gln Arg Ser
            100                 105                 110 agc tgg cct ccg gtg tac act ttt ggc cag ggg acc aag ctt gaa atc      384
Ser Trp Pro Pro Val Tyr Thr Phe Gly Gln Gly Thr Lys Leu Glu Ile
        115                 120                 125 aaa cga act gtg gct gca cca tct gtc ttc atc ttc ccg cca tct gat      432
Lys Arg Thr Val Ala Ala Pro Ser Val Phe Ile Phe Pro Pro Ser Asp
130                 135                 140 gag cag ttg aaa tct gga act gcc tct gtt gtg tgc ctg ctg aat aac      480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc      528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac      576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac      624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc      672
Glu Lys His Lys Val Tyr Ala Cys Glu Val Thr His Gln Gly Leu Ser
210                 215                 220 tcg ccc gtc aca aag agc ttc aac agg gga gag tgt tag                  711
Ser Pro Val Thr Lys Ser Phe Asn Arg Gly Glu Cys
225                 230                 235
```

<210> SEQ ID NO 20
<211> LENGTH: 469
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Met Ala Trp Val Trp Thr Leu Pro Phe Leu Met Ala Ala Ala Gln Ser
 1               5                  10                  15

Val Gln Ala Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110
```

```
Tyr Tyr Cys Ala Arg Leu Trp Phe Gly Asp Leu Asp Ala Phe Asp Ile
            115                 120                 125

Trp Gly Gln Gly Thr Met Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 21
<211> LENGTH: 1410
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
```

<221> NAME/KEY: CDS
<222> LOCATION: (1)..(1410)

<400> SEQUENCE: 21

```
atg gct tgg gtg tgg acc ttg cca ttc ctg atg gca gct gcc caa agt      48
Met Ala Trp Val Trp Thr Leu Pro Phe Leu Met Ala Ala Ala Gln Ser
1               5                   10                  15 gtc cag gca gaa gtg cag ctg gtg gag tct ggg gga ggc gtg gtc cag      96
Val Gln Ala Glu Val Gln Leu Val Glu Ser Gly Gly Gly Val Val Gln
            20                  25                  30 cct ggg agg tcc ctg aga ctc tcc tgt gca gcg tct gga ttc acc ttc     144
Pro Gly Arg Ser Leu Arg Leu Ser Cys Ala Ala Ser Gly Phe Thr Phe
        35                  40                  45 agt agc tat ggc atg cac tgg gtc cgc cag gct cca ggc aag ggg ctg     192
Ser Ser Tyr Gly Met His Trp Val Arg Gln Ala Pro Gly Lys Gly Leu
    50                  55                  60 gag tgg gtg gca att ata tgg tat gat gga agt aat aaa tac tat gcg     240
Glu Trp Val Ala Ile Ile Trp Tyr Asp Gly Ser Asn Lys Tyr Tyr Ala
65                  70                  75                  80 gac tcc gtg aag ggc cga ttc acc atc tcc aga gac aat tcc aag aac     288
Asp Ser Val Lys Gly Arg Phe Thr Ile Ser Arg Asp Asn Ser Lys Asn
                85                  90                  95 acg ctg tat ctg caa atg aac agc ctg aga gcc gag gac acg gct gtg     336
Thr Leu Tyr Leu Gln Met Asn Ser Leu Arg Ala Glu Asp Thr Ala Val
            100                 105                 110 tat tac tgt gcg agg cta tgg ttc ggg gac tta gat gct ttt gat atc     384
Tyr Tyr Cys Ala Arg Leu Trp Phe Gly Asp Leu Asp Ala Phe Asp Ile
        115                 120                 125 tgg ggc caa ggg aca atg gtc acc gtc tcc tca gcc tcc acc aag ggc     432
Trp Gly Gln Gly Thr Met Val Thr Val Ser Ser Ala Ser Thr Lys Gly
    130                 135                 140 cca tcg gtc ttc ccc ctg gca ccc tcc tcc aag agc acc tct ggg ggc     480
Pro Ser Val Phe Pro Leu Ala Pro Ser Ser Lys Ser Thr Ser Gly Gly
145                 150                 155                 160 aca gcg gcc ctg ggc tgc ctg gtc aag gac tac ttc ccc gaa ccg gtg     528
Thr Ala Ala Leu Gly Cys Leu Val Lys Asp Tyr Phe Pro Glu Pro Val
                165                 170                 175 acg gtg tcg tgg aac tca ggc gcc ctg acc agc ggc gtg cac acc ttc     576
Thr Val Ser Trp Asn Ser Gly Ala Leu Thr Ser Gly Val His Thr Phe
            180                 185                 190 ccg gct gtc cta cag tcc tca gga ctc tac tcc ctc agc agc gtc gtg     624
Pro Ala Val Leu Gln Ser Ser Gly Leu Tyr Ser Leu Ser Ser Val Val
        195                 200                 205 acc gtg ccc tcc agc agc ttg ggc acc cag acc tac atc tgc aac gtg     672
Thr Val Pro Ser Ser Ser Leu Gly Thr Gln Thr Tyr Ile Cys Asn Val
    210                 215                 220 aat cac aag ccc agc aac acc aag gtg gac aag aga gtt gag ccc aaa     720
Asn His Lys Pro Ser Asn Thr Lys Val Asp Lys Arg Val Glu Pro Lys
225                 230                 235                 240 tct tgt gac aaa act cac aca tgc cca ccg tgc cca gca cct gaa ctc     768
Ser Cys Asp Lys Thr His Thr Cys Pro Pro Cys Pro Ala Pro Glu Leu
                245                 250                 255 ctg ggg gga ccg tca gtc ttc ctc ttc ccc cca aaa ccc aag gac acc     816
Leu Gly Gly Pro Ser Val Phe Leu Phe Pro Pro Lys Pro Lys Asp Thr
            260                 265                 270 ctc atg atc tcc cgg acc cct gag gtc aca tgc gtg gtg gtg gac gtg     864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg     912
Ser His Glu Asp Pro Glu Val Lys Phe Asn Trp Tyr Val Asp Gly Val
```

```
gag gtg cat aat gcc aag aca aag ccg cgg gag gag cag tac aac agc      960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
            340                 345                 350 ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
        355                 360                 365 cag gtg tac acc ctg ccc cca tcc cgg gag gag atg acc aag aac cag     1152
Gln Val Tyr Thr Leu Pro Pro Ser Arg Glu Glu Met Thr Lys Asn Gln
    370                 375                 380 gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tat agc aag ctc     1296
Pro Pro Val Leu Asp Ser Asp Gly Ser Phe Phe Leu Tyr Ser Lys Leu
            420                 425                 430 acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
        435                 440                 445 gtg atg cat gag gct ctg cac aac cac tac acg cag aag agc ctc tcc     1392
Val Met His Glu Ala Leu His Asn His Tyr Thr Gln Lys Ser Leu Ser
    450                 455                 460 ctg tcc ccg ggt aaa tga                                             1410
Leu Ser Pro Gly Lys
465

<210> SEQ ID NO 22
<211> LENGTH: 51
<212> TYPE: DNA
<213> ORGANISM: Homo sapiens

<400> SEQUENCE: 22
gaaggttggc aggccaggga caacaycgtc tgccaagcca tggcagtaga c            51

<210> SEQ ID NO 23
<211> LENGTH: 51
<212> TYPE: DNA
<213> ORGANISM: Homo sapiens

<400> SEQUENCE: 23
taaggtattt ttgttatagc agcctrtatg gactaagctg acttgtaacg t            51

<210> SEQ ID NO 24
<211> LENGTH: 51
<212> TYPE: DNA
<213> ORGANISM: Homo sapiens

<400> SEQUENCE: 24
ctgtgtctgc agagcccaca cgtgtrtccc tgagaacaac ggaggcgcgg g            51

<210> SEQ ID NO 25
<211> LENGTH: 51
```

<212> TYPE: DNA
<213> ORGANISM: Homo sapiens

<400> SEQUENCE: 25
accccaggtc ccatatgtcc agagaktgtc cctccaatgg gaatgtgagg a         51

<210> SEQ ID NO 26
<211> LENGTH: 51
<212> TYPE: DNA
<213> ORGANISM: Homo sapiens

<400> SEQUENCE: 26
agggatgact tccaggaggg aagggmgggc attgtggccc ggctaacaga g         51

<210> SEQ ID NO 27
<211> LENGTH: 51
<212> TYPE: DNA
<213> ORGANISM: Homo sapiens

<400> SEQUENCE: 27
gtctcggccc ccaccagtgg ctatcrggag tttgtacatg cggtggagca g         51

<210> SEQ ID NO 28
<211> LENGTH: 51
<212> TYPE: DNA
<213> ORGANISM: Homo sapiens

<400> SEQUENCE: 28
gcaacagagg acatgaaaaa ttgctrtgac taaagcaggg acaatttgct g         51

<210> SEQ ID NO 29
<211> LENGTH: 51
<212> TYPE: DNA
<213> ORGANISM: Homo sapiens

<400> SEQUENCE: 29
cttgtatggg gaacccaaac ccagayggca gtttcttaa cctcttgcat c          51

<210> SEQ ID NO 30
<211> LENGTH: 51
<212> TYPE: DNA
<213> ORGANISM: Homo sapiens

<400> SEQUENCE: 30
gcttatgtca tcctgacacc tacgcrgatg tcggctcgaa tccactttgc c         51

<210> SEQ ID NO 31
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Thr Gln Arg Met Leu Ser Gly Phe Cys Pro His Lys Val Ser Ala
1               5                   10                  15

<210> SEQ ID NO 32
<211> LENGTH: 15
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 32

Met Leu Ser Gly Phe Cys Pro His Lys Val Ser Ala Gly Gln Phe
1               5                   10                  15

<210> SEQ ID NO 33
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Met Leu Ser Gly Phe Cys Pro His Lys Val Ser Ala
1               5                   10

<210> SEQ ID NO 34
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ser Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
                100                 105                 110

Phe Asn

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Pro Gly Pro Val Pro Pro Ser Thr Ala Leu Arg Glu Leu Ile
1               5                   10                  15

<210> SEQ ID NO 36
<211> LENGTH: 15
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 36

Pro Val Pro Pro Ser Thr Ala Leu Arg Glu Leu Ile Glu Glu Leu
1               5                   10                  15

<210> SEQ ID NO 37
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Pro Ser Thr Ala Leu Arg Glu Leu Ile Glu Glu Leu Val Asn Ile
1               5                   10                  15

<210> SEQ ID NO 38
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Ala Leu Arg Glu Leu Ile Glu Glu Leu Val Asn Ile Thr Gln Asn
1               5                   10                  15

<210> SEQ ID NO 39
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Glu Leu Ile Glu Glu Leu Val Asn Ile Thr Gln Asn Gln Lys Ala
1               5                   10                  15

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Glu Glu Leu Val Asn Ile Thr Gln Asn Gln Lys Ala Pro Leu Cys
1               5                   10                  15

<210> SEQ ID NO 41
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 41

Val Asn Ile Thr Gln Asn Gln Lys Ala Pro Leu Cys Asn Gly Ser
1               5                   10                  15

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Thr Gln Asn Gln Lys Ala Pro Leu Cys Asn Gly Ser Met Val Trp
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Lys Ala Pro Leu Cys Asn Gly Ser Met Val Trp Ser Ile Asn
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Pro Leu Cys Asn Gly Ser Met Val Trp Ser Ile Asn Leu Thr Ala
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asn Gly Ser Met Val Trp Ser Ile Asn Leu Thr Ala Gly Met Tyr
1               5                   10                  15

<210> SEQ ID NO 46
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Met Val Trp Ser Ile Asn Leu Thr Ala Gly Met Tyr Cys Ala Ala
1               5                   10                  15
```

```
<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ser Ile Asn Leu Thr Ala Gly Met Tyr Cys Ala Ala Leu Glu Ser
1               5                   10                  15

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Leu Thr Ala Gly Met Tyr Cys Ala Ala Leu Glu Ser Leu Ile Asn
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Met Tyr Cys Ala Ala Leu Glu Ser Leu Ile Asn Val Ser Gly
1               5                   10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Cys Ala Ala Leu Glu Ser Leu Ile Asn Val Ser Gly Cys Ser Ala
1               5                   10                  15

<210> SEQ ID NO 51
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Leu Glu Ser Leu Ile Asn Val Ser Gly Cys Ser Ala Ile Glu Lys
1               5                   10                  15

<210> SEQ ID NO 52
<211> LENGTH: 15
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Leu Ile Asn Val Ser Gly Cys Ser Ala Ile Glu Lys Thr Gln Arg
1               5                   10                  15

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Val Ser Gly Cys Ser Ala Ile Glu Lys Thr Gln Arg Met Leu Ser
1               5                   10                  15

<210> SEQ ID NO 54
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Cys Ser Ala Ile Glu Lys Thr Gln Arg Met Leu Ser Gly Phe Cys
1               5                   10                  15

<210> SEQ ID NO 55
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Ile Glu Lys Thr Gln Arg Met Leu Ser Gly Phe Cys Pro His Lys
1               5                   10                  15

<210> SEQ ID NO 56
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Phe Cys Pro His Lys Val Ser Ala Gly Gln Phe Ser Ser Leu
1               5                   10                  15

<210> SEQ ID NO 57
<211> LENGTH: 15
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 57

Pro His Lys Val Ser Ala Gly Gln Phe Ser Ser Leu His Val Arg
1               5                   10                  15

<210> SEQ ID NO 58
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Val Ser Ala Gly Gln Phe Ser Ser Leu His Val Arg Asp Thr Lys
1               5                   10                  15

<210> SEQ ID NO 59
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Gln Phe Ser Ser Leu His Val Arg Asp Thr Lys Ile Glu Val
1               5                   10                  15

<210> SEQ ID NO 60
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Ser Ser Leu His Val Arg Asp Thr Lys Ile Glu Val Ala Gln Phe
1               5                   10                  15

<210> SEQ ID NO 61
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

His Val Arg Asp Thr Lys Ile Glu Val Ala Gln Phe Val Lys Asp
1               5                   10                  15

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62
```

```
Asp Thr Lys Ile Glu Val Ala Gln Phe Val Lys Asp Leu Leu Leu
1               5                   10                  15
```

<210> SEQ ID NO 63
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

```
Ile Glu Val Ala Gln Phe Val Lys Asp Leu Leu Leu His Leu Lys
1               5                   10                  15
```

<210> SEQ ID NO 64
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

```
Ala Gln Phe Val Lys Asp Leu Leu Leu His Leu Lys Lys Leu Phe
1               5                   10                  15
```

<210> SEQ ID NO 65
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

```
Val Lys Asp Leu Leu Leu His Leu Lys Lys Leu Phe Arg Glu Gly
1               5                   10                  15
```

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

```
Leu Leu Leu His Leu Lys Lys Leu Phe Arg Glu Gly Arg Phe Asn
1               5                   10                  15
```

<210> SEQ ID NO 67
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

```
Phe Cys Pro His Lys Val
1               5
```